US 8,734,719 B2

United States Patent
Mototsu et al.

(10) Patent No.: US 8,734,719 B2
(45) Date of Patent: May 27, 2014

(54) PARTS SUPPLY DEVICE, SAMPLE ANALYZING DEVICE, PARTS SUPPLY METHOD

(75) Inventors: Kazunori Mototsu, Kobe (JP); Masayuki Nakagawa, Hyogo (JP)

(73) Assignee: Sysmex Corporation, Kobe (JP)

( * ) Notice: Subject to any disclaimer, the term of this patent is extended or adjusted under 35 U.S.C. 154(b) by 1254 days.

(21) Appl. No.: 11/716,165

(22) Filed: Mar. 9, 2007

(65) Prior Publication Data
US 2007/0212260 A1 Sep. 13, 2007

(30) Foreign Application Priority Data

Mar. 10, 2006 (JP) .................................. 2006-66787
Mar. 31, 2006 (JP) .................................. 2006-97111

(51) Int. Cl.
| | | |
|---|---|---|
| G01N 35/04 | (2006.01) | |
| B65G 47/14 | (2006.01) | |
| G01N 35/10 | (2006.01) | |
| B01L 9/00 | (2006.01) | |

(52) U.S. Cl.
CPC ............ *B65G 47/1478* (2013.01); *G01N 35/10* (2013.01); *G01N 35/04* (2013.01); *B01L 9/54* (2013.01); *G01N 2035/103* (2013.01)
USPC ............... 422/63; 422/64; 422/524; 221/171; 198/409

(58) Field of Classification Search
USPC ..................................... 422/63, 524; 221/171
See application file for complete search history.

(56) References Cited

U.S. PATENT DOCUMENTS

| | | | |
|---|---|---|---|
| 488,084 A | 12/1892 | Miner | |
| 2,515,404 A * | 7/1950 | Grosvenor ..................... | 198/786 |
| 3,086,639 A | 4/1963 | Donofrio | |
| 6,138,868 A * | 10/2000 | Yuyama et al. ........... | 221/312 R |
| 6,505,756 B1 | 1/2003 | Walldorf et al. | |
| 6,986,439 B2 | 1/2006 | Itoh | |
| 2003/0047418 A1* | 3/2003 | Okada et al. ............... | 198/459.1 |
| 2004/0005245 A1 | 1/2004 | Watson et al. | |
| 2004/0108330 A1 | 6/2004 | Itoh | |
| 2004/0109791 A1 | 6/2004 | Itoh | |
| 2007/0148042 A1* | 6/2007 | Ootani et al. ................... | 422/63 |

FOREIGN PATENT DOCUMENTS

| | | |
|---|---|---|
| EP | 1083136 A1 | 3/2001 |
| JP | 63-067543 U | 5/1988 |
| JP | 07-213586 A | 8/1995 |
| JP | 08-324759 * | 12/1996 |

(Continued)

OTHER PUBLICATIONS

European Search Report for European Application No. 07004663.6, dated Sep. 15, 2009, 2 pages.

*Primary Examiner* — Kathryn Wright
(74) *Attorney, Agent, or Firm* — Brinks Gilson & Lione

(57) ABSTRACT

A parts supply device for supplying disposable part selected from a cuvette and pipette tip, comprising: a storage section for storing a plurality of disposable parts; a sort section for sorting the disposable parts supplied from the storage section, the sort section including a push-up plate to be capable of pushing up the disposable part in the supplied parts and a wall section arranged at the downstream side of the push-up plate so as to be adjacent to the push-up plate, wherein the push-up plate is configured to vertically move along the wall section between a first position and a second position that is above the first position; and a transfer section for transferring one by one the disposable part supplied by the push-up plate over the wall section.

17 Claims, 28 Drawing Sheets

(56) References Cited

FOREIGN PATENT DOCUMENTS

| JP | 08-324759 | A |   | 12/1996 |
|----|-----------|---|---|---------|
| JP | 08324759  | A | * | 12/1996 |
| JP | 10-062433 |   |   | 3/1998  |
| JP | 2000-019182 |   |   | 1/2000 |
| JP | 200019182 | A | * | 1/2000 |
| JP | 2001-187629 | A |   | 7/2001 |
| JP | 2002-326716 | A |   | 11/2002 |
| JP | 2002036716 | A | * | 11/2002 |
| JP | 2003-083999 |   |   | 3/2003 |

\* cited by examiner

PARTS SUPPLY DEVICE, SAMPLE ANALYZING DEVICE, PARTS SUPPLY METHOD

RELATED APPLICATIONS

This application claims priority under 35 U.S.C. §119 to Japanese Patent Application Nos. JP2006-66787 filed Mar. 10, 2006, and JP2006-97111 filed Mar. 31, 2006, the entire content of which is hereby incorporated by reference.

FIELD OF THE INVENTION

The present invention relates to a supply device for supplying parts such as pipette tips or cuvettes used for analyzing a specimen such as blood, serum, or urine, a supply method, a sample analyzing device provided with the supply device.

BACKGROUND OF THE INVENTION

An automatic dispensing tip supply device capable of supplying plural dispensing tips (pipette tips) one by one has conventionally been known (e.g., see U.S. 2004108330). The automatic dispensing tip supply device disclosed in the U.S. 2004108330 is composed of a storage box for storing a dispensing tip, a tip individual sending mechanism for sending one by one the plural dispensing tips stored in the storage box, and a door mechanism having a tip holding part that can horizontally hold one dispensing tip. A push-up plate having an upper end surface on which only one dispensing tip can be placed laterally is provided at the tip individual sending mechanism of the automatic dispensing tip supply device. This push-up plate is vertically driven, whereby the dispensing tip placed on the upper end surface of the push-up plate is directed to the tip holding part of the door mechanism section. Then, the dispensing tip held by the tip holding part is discharged to the outside by opening the door of the door mechanism.

However, the dispensing tip used in the automatic dispensing tip supply device disclosed in U.S. 2004108330 has a base portion having a large diameter and a leading end having a small diameter and generally conic shape. Therefore, there may be the case in which two dispensing tips are arranged on the upper end surface of the push-up plate as vertically overlapped in the opposite direction. In this case, two dispensing tips overlapped in the opposite direction are disadvantageously pushed up as arranged on the upper surface of the push-up plate. As a result, two dispensing tips might simultaneously be discharged to the outside.

A pipette tip or cuvette is conventionally used in an analyzing device for analyzing specimen such as blood or serum. For example, a system in which a rack having pipette tips accommodated therein is mounted as a system for supplying pipette tips to a dispensing device has been used (see Japanese Unexamined Patent Publication No. HEI10-62433). The device described above needs a labor for accommodating pipette tips into the rack. U.S. Pat. No. 6,986,439 discloses a tip positioning and storing device that automates the accommodation of pipette tips into the rack, for example.

In the system using the rack, it is generally necessary to set plural racks to the device. Therefore, a space for plural racks are required. Further, a rack supply mechanism and discharge mechanism should further be provided in order to enhance processing capacity, thereby increasing the size of the device.

In view of this, there has been proposed a supply device in which parts such as pipette tips or cuvettes are unintentionally accommodated into an accommodating chamber, parts are automatically aligned, and parts are supplied to a predetermined position one by one.

For example, Japanese Unexamined Patent Publication No. 2000-19182 and Japanese Unexamined Patent Publication No. 2003-83999 disclose a device in which a conveyer scoops up parts such as pipette tips or cuvettes accommodated in the accommodating chamber, and the scooped parts are dropped to a funnel-shaped guide for aligning the parts.

Meanwhile, parts such as pipette tips or cuvettes are exchanged for each analysis in an analyzing device, so that it is desired that a great number of parts, e.g., several hundred parts, can be accommodated into an accommodating chamber. However, in the above-mentioned device in which the conveyer scoops up the parts one by one from the accommodating chamber, when a great number of parts are accommodated into the accommodating chamber, it becomes difficult to scoop up the parts one by one by the conveyer due to the weight or interference of the great number of parts.

SUMMARY OF THE INVENTION

The scope of the present invention is defined solely by the appended claims, and is not affected to any degree by the statements within this summary.

A parts supply device according to a first aspect of the present invention is a parts supply device for supplying disposable part selected from a cuvette and pipette tip, comprising: a storage section for storing a plurality of disposable parts; a sort section for sorting the disposable parts supplied from the storage section, the sort section including a push-up plate to be capable of pushing up the disposable part in the supplied parts and a wall section arranged at the downstream side of the push-up plate so as to be adjacent to the push-up plate, wherein the push-up plate is configured to vertically move along the wall section between a first position and a second position that is above the first position; and a transfer section for transferring one by one the disposable part supplied by the push-up plate over the wall section.

A parts supply device according to a second aspect of the present invention is a parts supply device for supplying disposable part selected from a cuvette and pipette tip, comprising: a part accommodating section which accommodates a plurality of disposable part and sends a predetermined amount of accommodated disposable parts, the part accommodating section including a holding member to be capable of holding the disposable parts; and a part sort section for sorting the sent disposable part in the sent disposable parts, wherein the holding member which divides and sends the predetermined amount of accommodated disposable part from the part accommodating section to the part sort section.

A parts supply method according to a third aspect of the present invention is a parts supply method for supplying parts selected from a cuvette and pipette tip, the method comprising steps of: dividing a predetermined amount of disposable part accommodated in a part accommodating section; sending the divided disposable part from the part accommodating section; sorting the sent disposable part one by one.

DETAILED DESCRIPTION OF THE PREFERRED EMBODIMENT

The embodiments of the present invention will now be described based on the drawings.

First, the configuration of an immune analyzing device equipped with a pipette tip supply device according to one embodiment of the present invention will now be described with reference to FIGS. 1 to 29 and FIGS. 38a to 38c.

Figure 1:
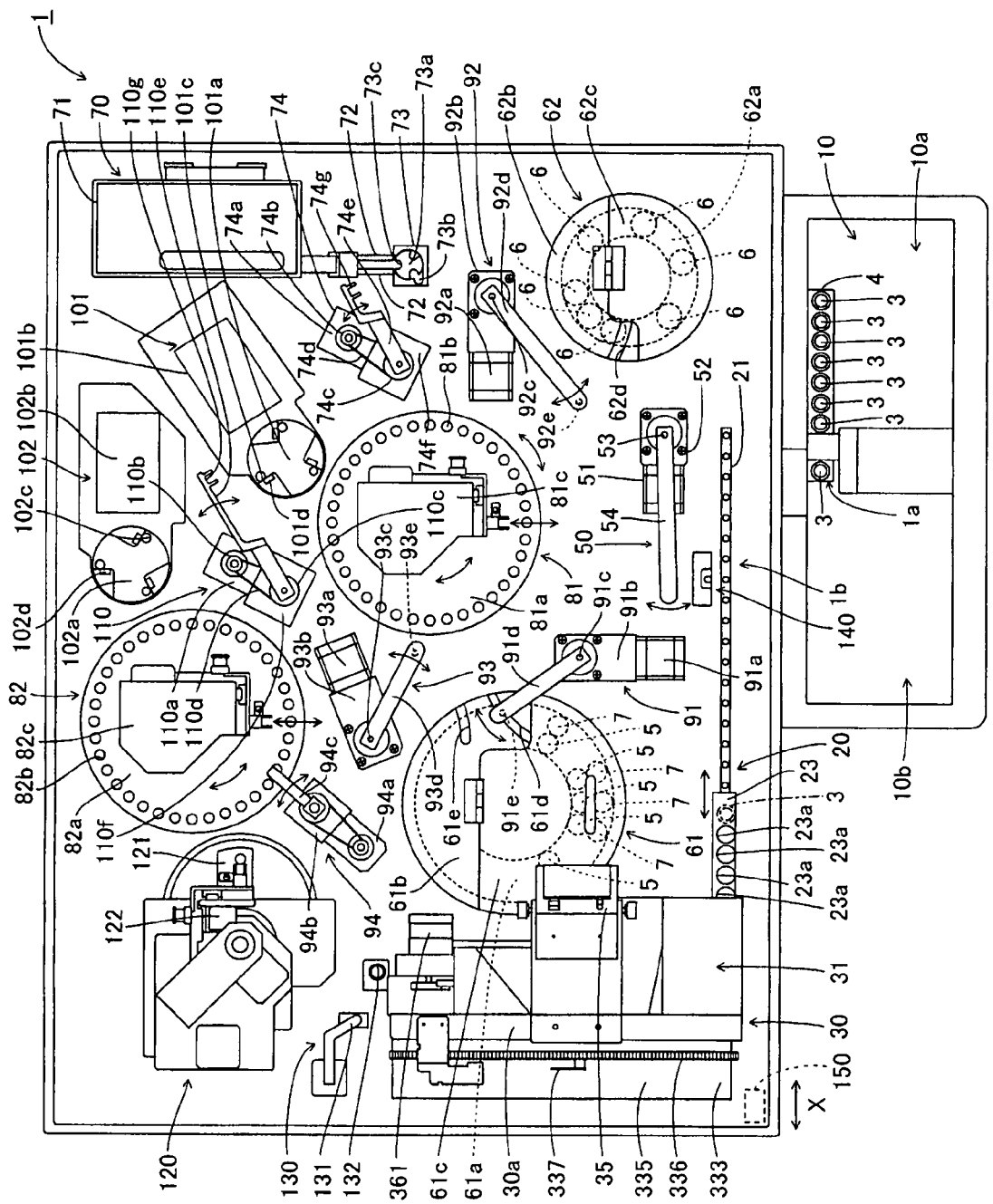
FIG. 1 is a plan view showing an overall configuration of an immune analyzing device provided with an automatic pipette tip supply device according to one embodiment of the present invention.

The immune analyzing device 1 equipped with a pipette tip supply device 30 according to one embodiment of the present invention is a device for performing examination on various items such as hepatitis B, hepatitis C, tumor marker, thyroid hormone and the like using specimens such as blood. The immune analyzing device 1 is configured by a control section 401, a specimen conveying section (sampler) 10, an emergency specimen and tip conveying section 20, a pipette tip supply device 30, a specimen dispensing arm 50, reagent installing sections 61 and 62, a cuvette supply section 70, a primary reaction section 81 and a secondary reaction section 82, reagent dispensing arms 91, 92, 93 and 94, a BF separating section 101 and a BF separating section 102, a conveyance catcher 110, a detecting section 120, a disposing section 130, and a tip releasing section 140, as shown in FIG. 1. In the immune analyzing device 1 according to the present embodiment, the disposable pipette tip 2 (see FIG. 2) is replaced each time suction and discharge of the specimen are performed to suppress the specimen such as blood suctioned and discharged by the specimen dispensing arm 50 from mixing with other specimen.

In the immune analyzing device 1, after the specimen such as blood containing antigen, which is the measurement target, trapped antibody (R1 reagent), magnetic particles (R2 reagent) are mixed, and the antigen, trapped antibody and magnetic particles are bound, the magnetic particles are attracted to a magnet 101d of the BF (Bound Free) separating section 101 thereby removing the solution containing non-reacting (Free) trapped antibody. After binding a labeled antibody (R3 reagent) to the magnetic particles bound with antigen, the bound magnetic particles, antigen, and labeled antibody are attracted to the magnet 102d of the BF separating section 102 thereby removing the R3 reagent containing the non-reacting (free) labeled antibody. Furthermore, after adding a light emitting substrate (R5 reagent) that emits light in the reaction process with the labeled antibody, the light emission amount produced by the reaction between the labeled antibody and the light emitting substrate is measured. The antigen contained in the specimen that binds with the labeled antibody is quantitatively measured through such process.

The specimen conveying section 10 is configured so as to convey a rack 4 mounted with a plurality of test tubes 3 accommodating the specimen to a position corresponding to the suction position 1a of the specimen dispensing arm 50 as shown in FIG. 1. The specimen conveying section 10 includes a rack set part 10a for setting the rack 4 mounted with the test tube 3 accommodating non-processed specimens, and a rack storage part 10b for storing the rack 4 mounted with the test tube 3 accommodating the dispense processed specimens. When the test tube 3 accommodating the non-processed specimen is conveyed to the position corresponding to the suction position 1a of the specimen dispensing arm 50, the specimen such as blood in the test tube 3 is suctioned by the specimen dispensing arm 50 and the rack 4 mounted with the relevant test tube 3 is stored in the rack storage part 10b.

Figure 3:
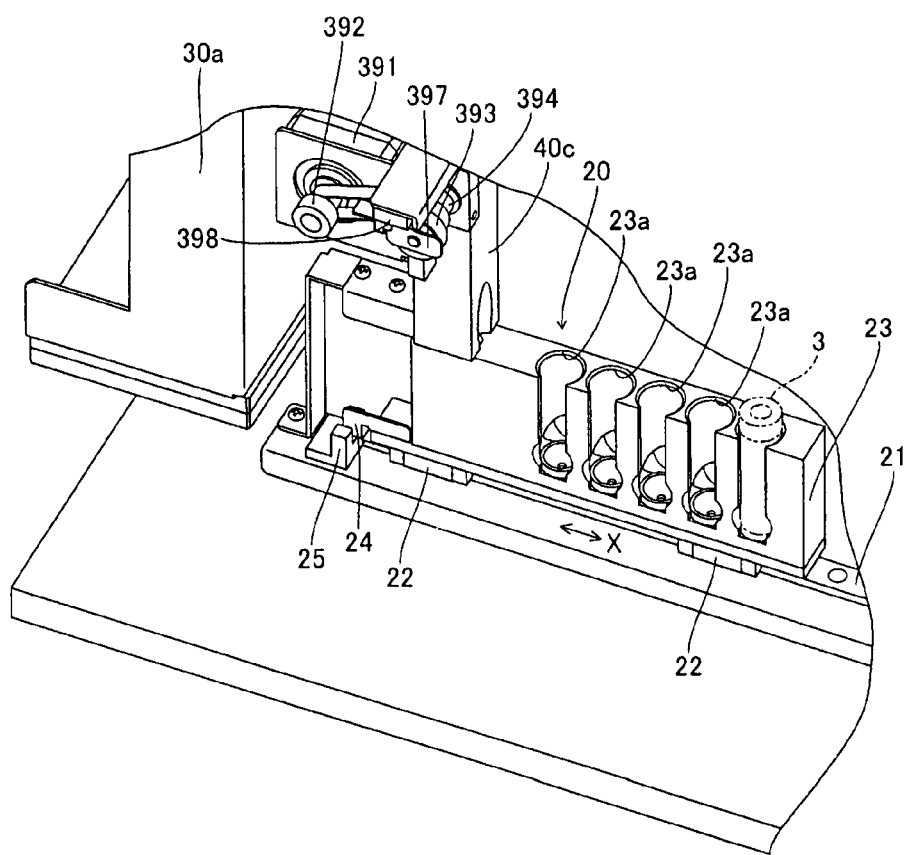
FIG. 3 is a perspective view showing an emergency specimen and tip conveying section in the immune analyzing device shown in FIG. 1.
Figure 4:
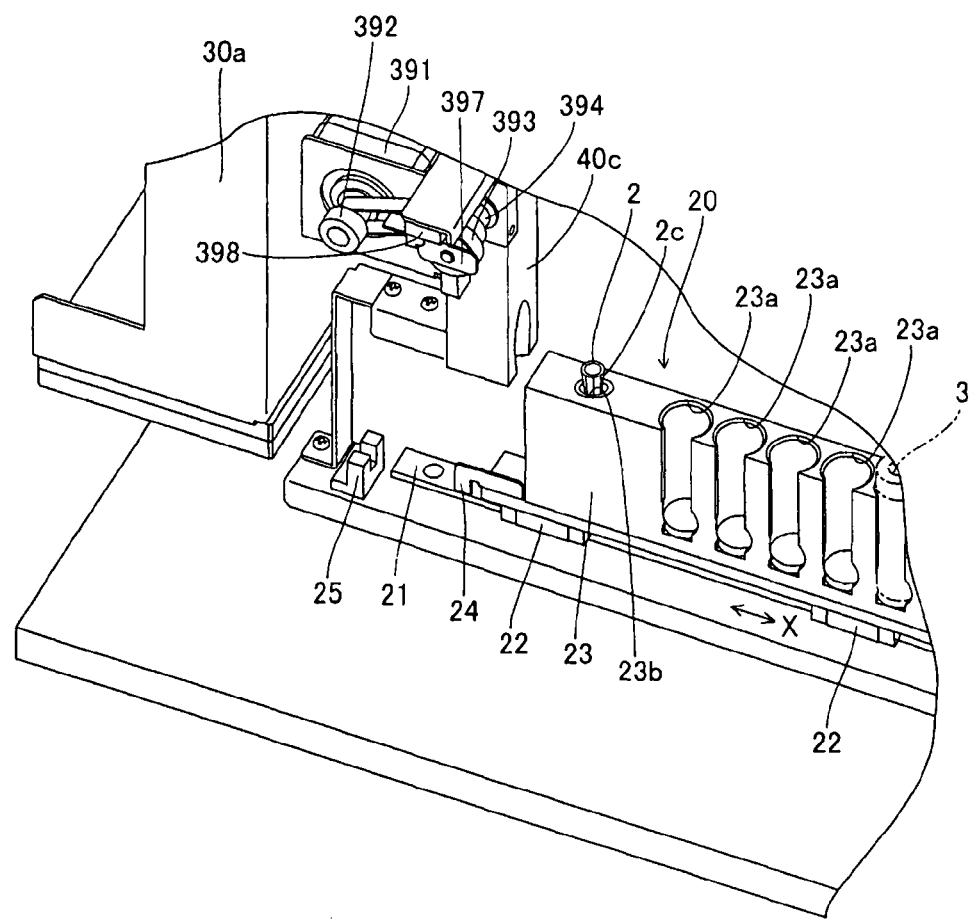
FIG. 4 is a perspective view showing an emergency specimen and tip conveying section in the immune analyzing device shown in FIG. 1.

The emergency specimen and tip conveying section 20 is configured so as to convey the test tube 3 accommodating emergency specimens, which must cut into the specimens being conveyed by the specimen conveying section 10 and examined, to an attachment position 1b of the specimen dispensing arm 50. As shown in FIGS. 1, 3, and 4, the emergency specimen and tip conveying section 20 includes a slide rail 21 arranged so as to extend in the X direction, a linear moving guide including a slide main body 22 arranged movable along the slide rail 21, a conveying rack 23 attached to the slide main body 22, a detection strip 24 attached to the lower part of the conveying rack 23, and a light shielding sensor 25 light shielded by the detection strip 24. Furthermore, the conveying rack 23 is arranged with a test tube installing part 23a for installing the test tube 3 accommodating the emergency specimens, and a tip installing part 23b (see FIG. 4) of a long hole for mounting the pipette tip 2 (see FIG. 2) supplied from the pipette tip supply device 30 to be hereinafter described. The detection strip 24 is arranged so as to light shield the light shielding sensor 25 when arranged at a position of receiving the pipette tip 2 from the pipette tip supply device 30. The conveying rack 23 conveys the test tubes 3 accommodating the emergency specimens and the pipette tip 2 to the attachment position 1b (see FIG. 1) of the specimen dispensing arm 50 by being moved along the slide rail 21 by the driving force from the motor (not shown).

Figure 5:
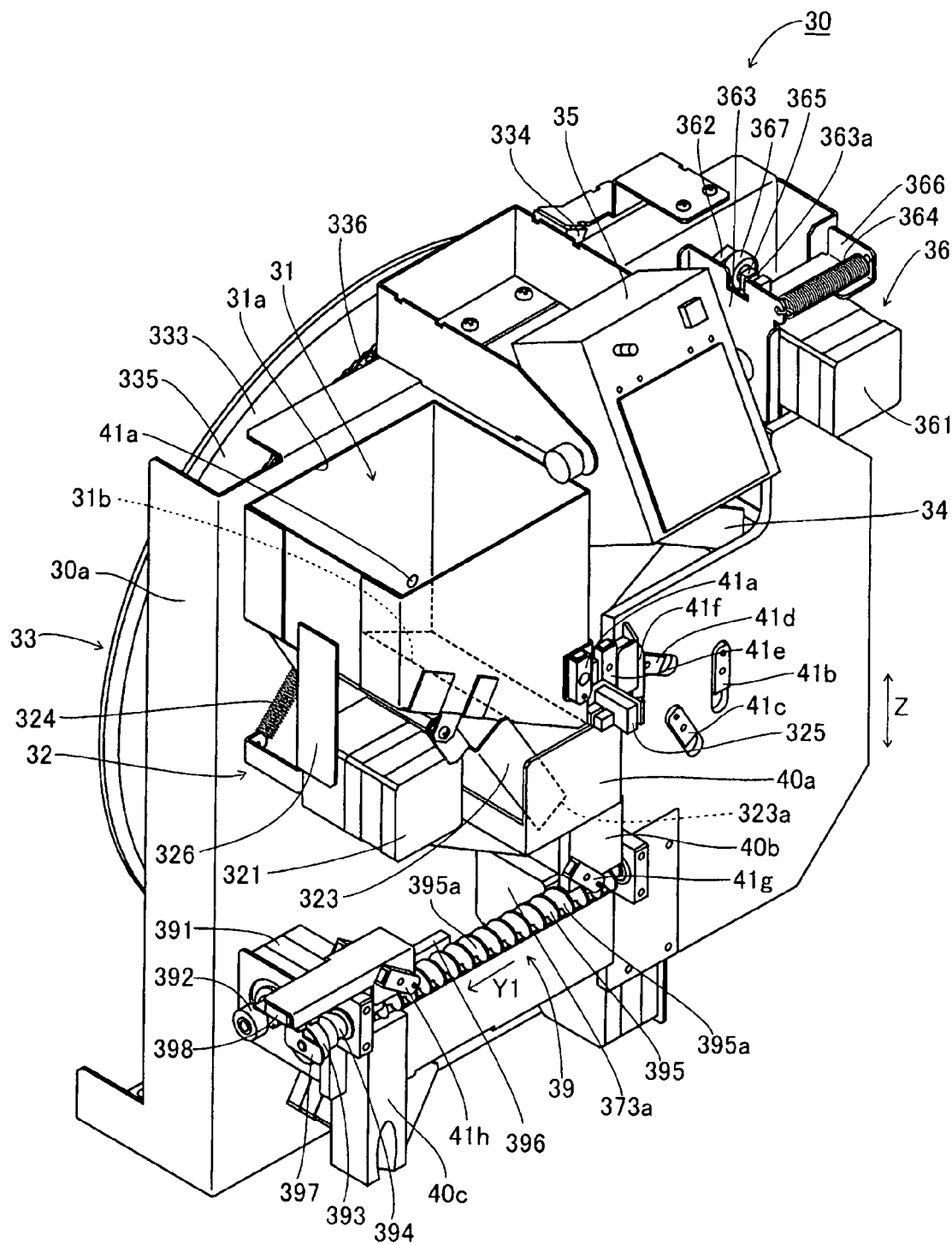
FIG. 5 is a perspective view showing an overall configuration of the automatic pipette tip supply device according to one embodiment of the present invention.
Figure 6:
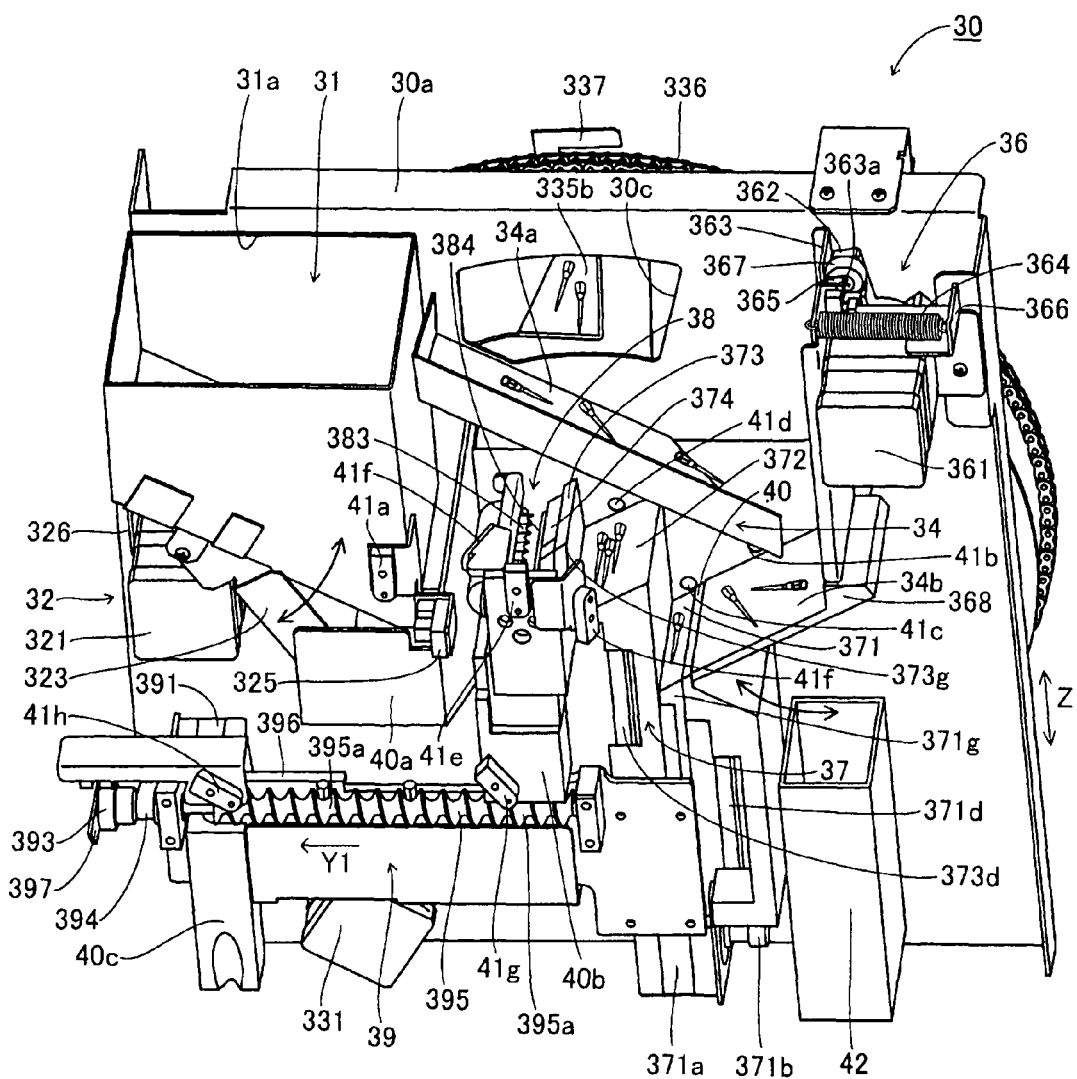
FIG. 6 is a perspective view showing an overall configuration of the automatic pipette tip supply device according to one embodiment shown in FIG. 5.

In the present embodiment, the pipette tip supply device 30 (see FIG. 1) has a function of installing one at a time the pipette tip (see FIG. 2) input to a tip refill section 31 to be hereinafter described to the tip installing part 23b of the conveying rack 23 of the emergency specimen and tip conveying section 20. Furthermore, the pipette tip supply device 30 also has a function of supplying the pipette tip to the tip installing part 23b of the conveying rack 23 with the distal end 2a of the pipette tip 2 facing downward. The pipette tip supply device 30 is configured by the tip refill section 31, a turning mechanism section 32, a tip supply mechanism section 33, a conveying path 34, a neutralizing fan 35, a discharge mechanism section 36, a sort mechanism section 37, a movement section 38 and a movement section 39, three shoots 40a to 40c, nine detection sensors (transmissive sensor) 41a to 41h, and a tip collecting container 42, as shown in FIGS. 5 and 6.

Figure 2:
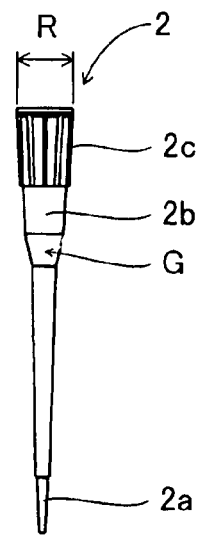
FIG. 2 is a front view of a pipette tip supplied by the automatic pipette tip supply device according to one embodiment of the present invention.

The tip refill section 31 is configured to be capable of accommodating plural disposable pipette tips 2 (see FIG. 2). The pipette tip 2 accommodated in the tip refill section 31 is commercially available in such a manner that plural pipette tips 2 (e.g., 500 pipette tips) are bagged. It has been known that the bagged pipette tips 2 carry static electric charges of about 6 kV during the transportation process for appearing on the market due to the rub against each other. As shown in FIG. 5, the tip refill section 31 includes an input port 31a into which plural pipette tips 2 taken from the bag are casually input, and a discharge port 31b from which the accommodated pipette tips 2 are discharged. The pipette tip 2 has, as shown in FIG. 2, a distal end 2a, body part 2b, and attachment part 2c, and it is formed such that the outer diameter and inner diameter are reduced toward the distal end 2a from the attachment part 2c. Therefore, the position of center of gravity G of this pipette tip 2 is shifted toward the attachment part 2c having the greater outer diameter and inner diameter.

A detection sensor (transmissive sensor) 41a for detecting the presence of the pipette tip 2 accommodated in the tip refill section 31 is arranged at a position in the vicinity of the discharge port 31b of the tip refill section 31.

A shoot 40a for leading the pipette tips 2 dropped from the discharge port 31b to a drum 335 of the tip supply mechanism section 33 to be hereinafter described through an opening 30b (see FIG. 8) of a chassis 30a is arranged at a position of receiving the pipette tip 2 dropped from the discharge port 31b of the tip refill section 31.

Figure 7:
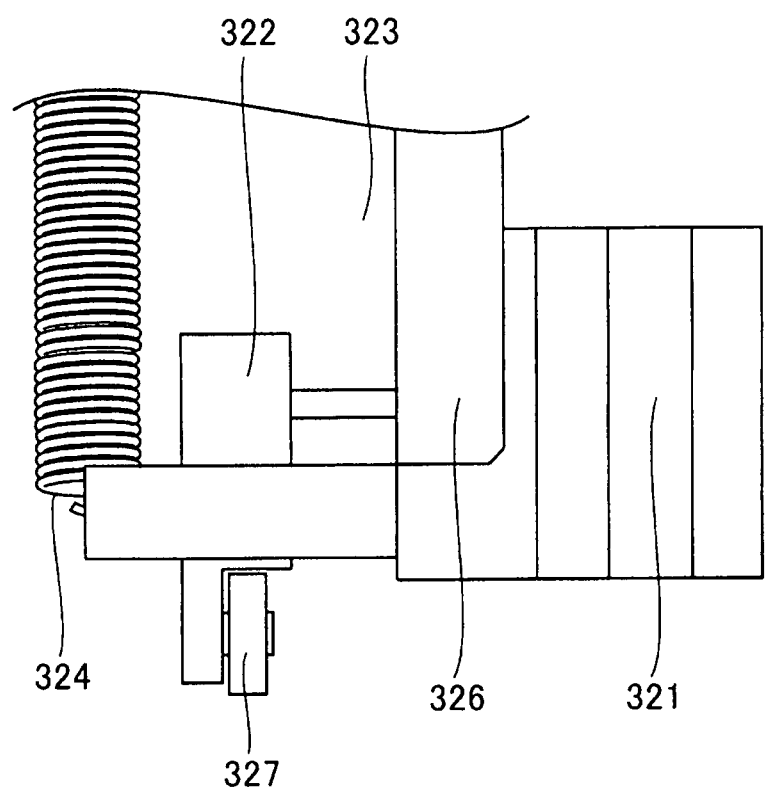
FIG. 7 is a side view showing a turning mechanism section of the automatic pipette tip supply device according to one embodiment shown in FIG. 5.

The turning mechanism section 32 is configured so as to turn the turning member 323 from a position of blocking the discharge port 31b of the tip refill section 31 to a position of opening the discharge port 31b. The turning mechanism section 32 is configured by a motor 321 acting as a driving source, a pressing member 322 attached to the motor 321, a turning member 323 pressed against the pressing member 322, an extension coil spring 324, and a light shielding sensor 325 (see FIGS. 5 and 6), as shown in FIGS. 6 and 7. The motor 321 is attached to a steel plate 326 attached to the tip refill section 31. One end of the extension coil spring 324 is attached to the steel plate 326, and the other end of the extension coil spring 324 is attached to the turning member 323. In other words, the extension coil spring 324 is arranged so as to bias the turning member 323 in a direction of moving away from the position of blocking the discharge port 31b. A roller 327 for pressing the turning member 323 is attached to the pressing member 322. The light shielding sensor 325 is arranged so as to detect the side surface 323a (see FIG. 5) of the turning member 323 when the turning member 323 is turned to the position of blocking the discharge port 31b.

Figure 8:
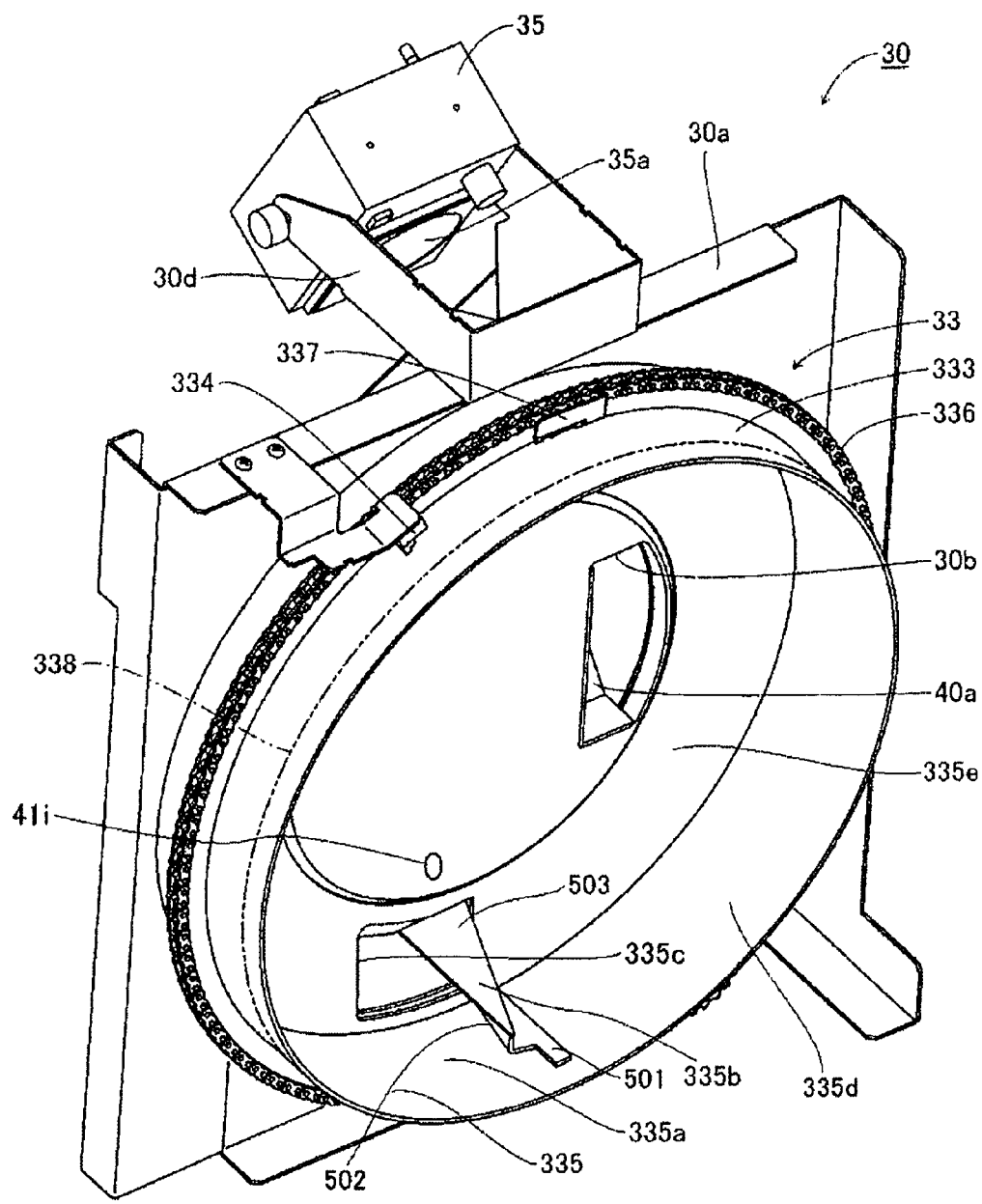
FIG. 8 is a perspective view of the automatic pipette tip supply device, seen from a tip refill mechanism section, according to one embodiment shown in FIG. 5.
Figure 9:
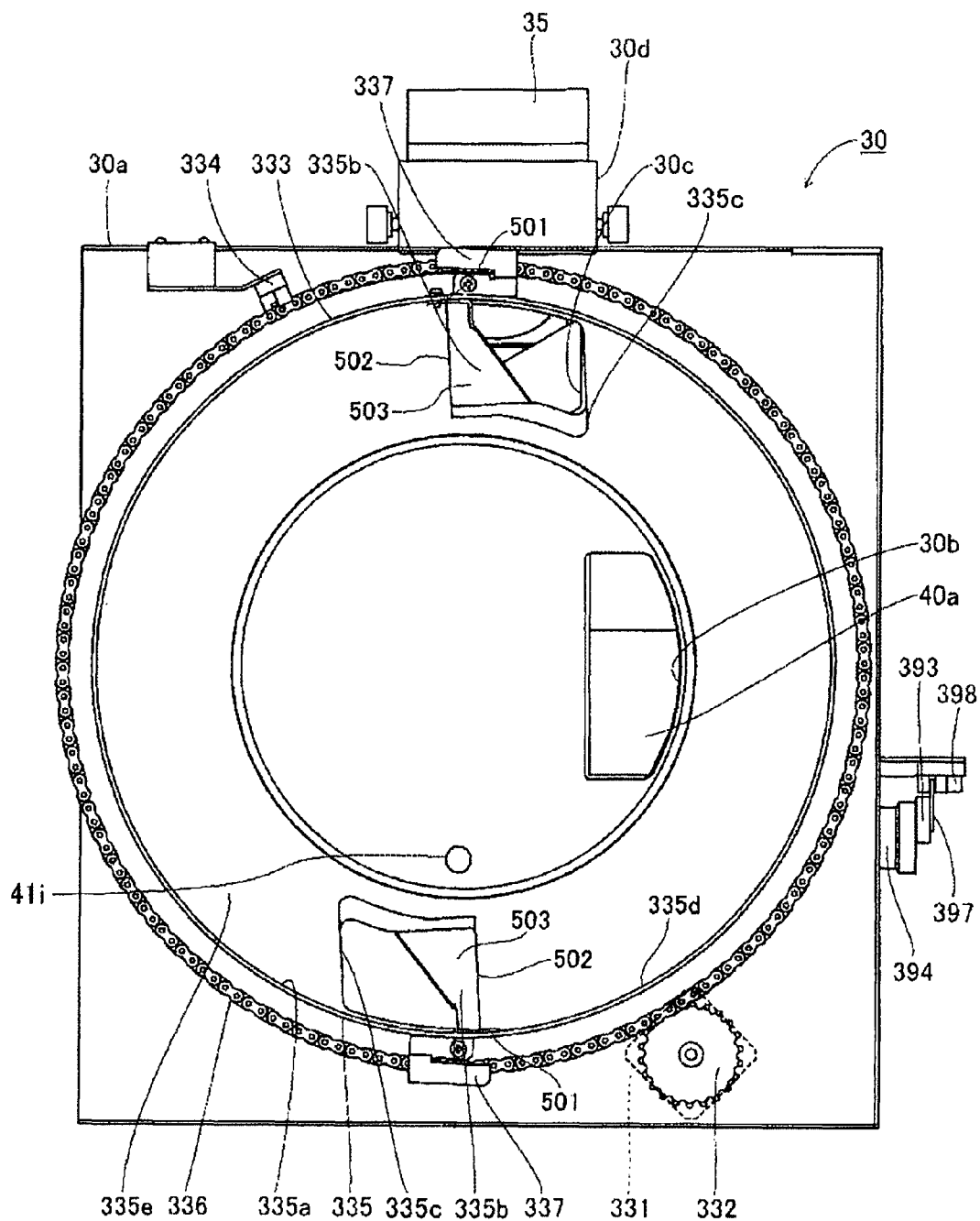
FIG. 9 is a front view of the automatic pipette tip supply device, seen from a tip refill mechanism section, according to one embodiment shown in FIG. 5.

As shown in FIGS. 8 and 9, the tip supply mechanism section 33 has a function of receiving the pipette tip 2 input through the shoot 40a and the opening 30b of the chassis 30a from the discharge port 31b of the tip refill section 31 and sending some of the received pipette tips 2 to the conveying path 34 to be hereinafter described. The tip supply mechanism section 33 is configured by a stepping motor 331 acting as a driving source, a gear 332 attached to the stepping motor 331, a drum part 333 rotatably attached to the chassis 30a, and a light shielding sensor 334 for detecting the rotating position of the drum part 333. The drum part 333 includes a drum 335 made up of a tubular body capable of accommodating the plurality of pipette tips 2, a chain 336 winded to the periphery of the drum 335 so as to gear with the gear 332, two detection strips 337 detected by the light shielding sensor 334, and a lid 338 (see FIG. 8) attached on the opposite side of the chassis 30a side so as to block the accommodating part 335a of the drum 335 of the tubular body. Two segmenting parts 335b capable of lifting the pipette tips 2 when the drum part 33 rotates are arranged at an interval of 180 degrees on the inner side of the drum 335. The segmenting part 335b has the size and the shape of having the number of pipette tips 2 to be sent to the conveying path 34 to be of a predetermined number (5 to 15 in the present embodiment), and is arranged so as not to send the pipette tips 2 to the conveying path 34 in excess amount. Thus, when the gear 332 rotates by the drive of the stepping motor 331, the chain 336 geared to the gear 332 and the drum 335 winded with the chain 336 rotate. The segmenting part 335b arranged on the inner side of the drum 335 also rotates with the rotation of the drum 335, and the pipette tips 2 accumulated at the lower part in the accommodating part 335a of the drum 335 are lifted by the segmenting part 335b and sent to the conveying path 34 to be hereinafter described through the opening 30c (see FIG. 6) of the chassis 30a.

Subsequently, the configuration of the tip supply mechanism section 33 will be explained in detail. The pipette tip 2 taken out of a bag by a user is inputted into the tip refill section 31, and then, discharged from the discharge port 31b. The tip supply mechanism section 33 is configured to receive the pipette tip 2 thus discharged through the shoot 40a (see FIG. 5) and the opening 30b (see FIG. 8) of the chassis 30a and to send some of the received pipette tips 2 to the conveying path 34 to be hereinafter described. The tip supply mechanism section 33 includes, as shown in FIGS. 8 and 9, a stepping motor 331 acting as a driving source, a gear 332 attached to the stepping motor 331, a drum part 333 rotatably attached to the chassis 30a, and a light shielding sensor 334 for detecting the rotating position of the drum part 333. The drum part 333 includes a drum 335 made up of a tubular body having a center axis extending horizontally and capable of accommodating the plurality of pipette tips 2, a chain 336 winded to the periphery of the drum 335 so as to gear with the gear 332, two detection strips 337 detected by the light shielding sensor 334, and a lid 338 (see FIG. 8) attached on the opposite side of the chassis 30a side so as to block the accommodating part 335a of the drum 335 of the tubular body. A detection sensor (transmissive sensor) 41i for detecting the accommodating amount of the pipette tip 2 accommodated into the drum 335 is disposed at the inner wall of the drum 335 in the vicinity of the section above the segmenting part 335b described later. When the gear 332 rotates by the drive of the stepping motor 331, the chain 336 geared to the gear 332 and the drum 335 winded with the chain 336 rotate about the center axis (rotational axis) of the drum 335 as the center of the rotation.

The chassis 30a is disposed at the side face of the drum 335, opposite to the side of the lid 338 (see FIG. 8), so as to be in proximate contact with the side face of the drum 335. The opening 30c (see FIG. 6) of the chassis 30a is formed above the rotational axis of the drum 335. On the other hand, two openings 335c are formed at the side face of the drum 335 at the chassis 30a side at an interval of 180 degrees around the rotational axis of the drum 335, wherein the opening 335c and the opening 30c of the chassis 30a agree with each other by the rotation of the drum 335. When the openings 335c and the opening 30c of the chassis 30a do not agree with each other, the openings 335c are covered by the chassis 30a. The segmenting parts 335b are respectively provided on the inner side of the drum 335 at the vicinity of two openings 335c. The segmenting parts 335b extend toward the lid 338 from the edge of the opening 335c, opposite to the edge in the rotating direction of the drum 335, and its periphery. Specifically, the opening 335c is positioned at the side of the rotating direction of the drum 355 from the segmenting part 335b. More specifically, the segmenting part 335b is composed of a mounting part 501 attached to the inner peripheral surface 335d of the drum 335, a first support part 502 formed so as to rise toward the center of the rotation of the drum 335 from the mounting part 501, and a second support part 503 formed so as to bend toward the opening 335c from the end portion of the first support part 502 at the side of the center of the drum 335. The opening 335c has an almost rectangular shape longer in the rotating direction of the drum 335. The first support part 502 extends toward the lid 338 from the short side of the opening 335c opposite to the short side in the rotating direction. The second support part 503 extends toward the lid 338 from the long side of the opening 335c at the side of the rotational axis of the drum 335. The first support part 502 and the second support part 503 of the segmenting part 335b and the portion of the inner peripheral surface 335d of the drum 335 opposite to the second support part 503 form a space, and a predetermined amount (five to fifteen in this embodiment) of the pipette tips 2 can be retained in this space by the segmenting part 335b. Since the segmenting parts 335b are provided at the inner side of the drum 335, the segmenting parts 335b also rotate with the rotation of the drum 335.

Figure 38:
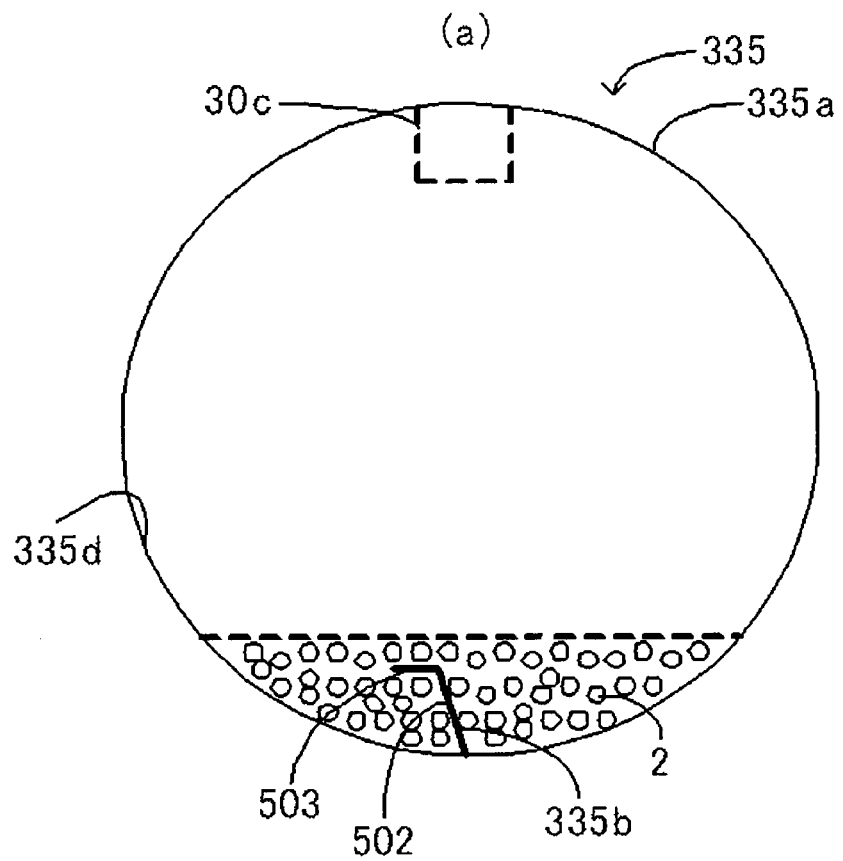
FIG. 38a is a schematic view for explaining the rotational movement of the segmenting part 335b in the drum 335 shown in FIG. 8.
FIG. 38b is a schematic view for explaining the rotational movement of the segmenting part 335b in the drum 335 shown in FIG. 8.
FIG. 38c is a schematic view for explaining the rotational movement of the segmenting part 335b in the drum 335 shown in FIG. 8.
FIG. 38d is a schematic view for explaining the rotational movement of the segmenting part 335b in the drum 335 shown in FIG. 8.
Figure 38:
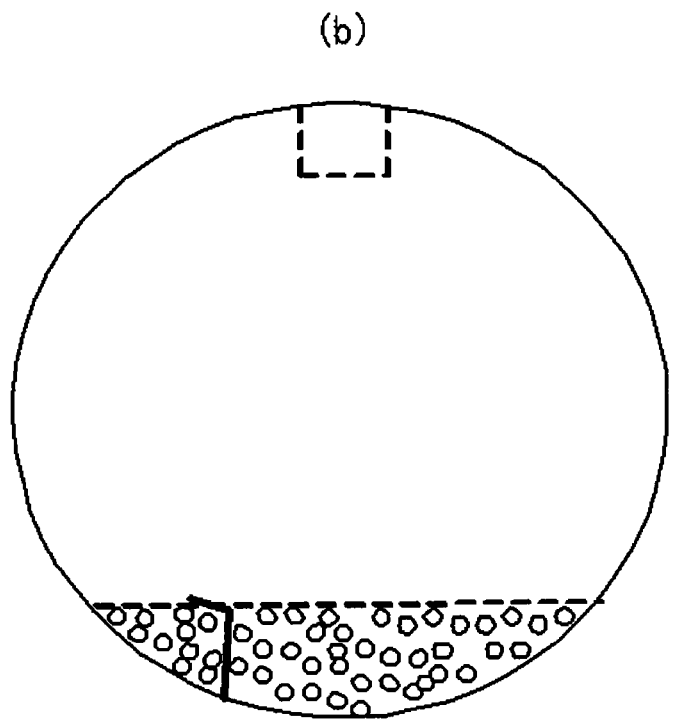
Figure 38:
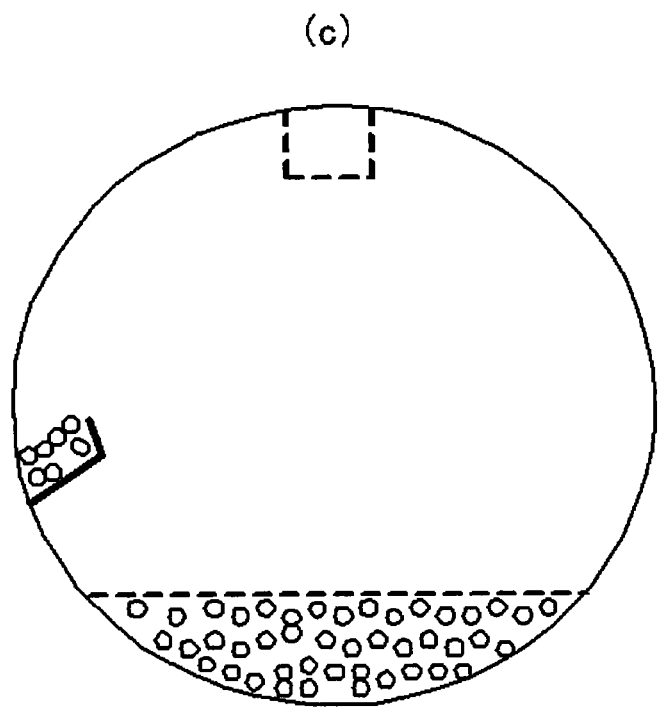
Figure 38:
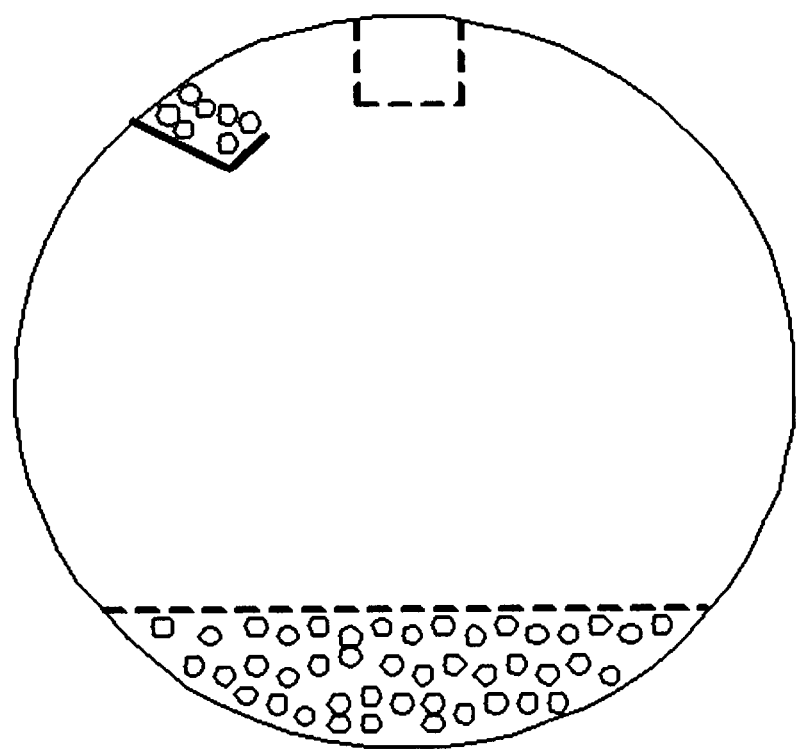

FIGS. 38a, 38b, 38c, and 38d are schematic views showing the state in which the segmenting part 335b rotates and moves in the drum 335, with the rotation of the drum 335, in the order of FIGS. 38a, 38b, 38c, and 38d. FIG. 38a shows that the segmenting part 335b is positioned at the lowermost part of the drum 335. As shown in FIG. 38a, some of the pipette tips 2 in the drum 335 are held by the segmenting part 335b. More specifically, some of the pipette tips 2 in the drum 335 are held by the space formed by the segmenting part 335b and the inner peripheral surface 335d. This space is formed at the position proximate to the opening 335c of the segmenting part 335b in the rotating direction of the drum 335. FIG. 38b shows that the segmenting part 335b rotates and moves from the position shown in FIG. 38a with the rotation of the drum 335. As shown in FIG. 38b, the segmenting part 335b starts to lift the pipette tips 2 held by the segmenting part 335b with the rotation. FIG. 38c shows that the segmenting part 335b rotates and moves from the position shown in FIG. 38*b* with the rotation of the drum 335. The segmenting part 335*b* has such a size and a shape as to have a predetermined amount (five to fifteen in this embodiment) of the pipette tips 2, so that the segmenting part 335*b* scoops up the predetermined amount of pipette tips 2 with the rotation so as to separate the predetermined amount of the pipette tips 2 from the pipette tips 2 accumulated at the lower part of the accommodating part 335*a* of the drum 335 as shown in FIG. 38*a*. The pipette tips 2 not separated still remain at the lower part in the accommodating part 335*a* of the drum 335. FIG. 38*d* shows that the segmenting part 335*b* rotates and moves from the position shown in FIG. 38*c* to the vicinity of the opening 30*c* of the chassis 30*a* with the rotation of the drum 335. As shown in FIG. 38*d*, the pipette tips 2 scooped up by the segmenting part 335*b* are conveyed to the opening 30*c* of the chassis 30*a*.

In the present embodiment, when the opening 335*c* and the opening 30*c* of the chassis 30*a* agree with each other with the rotation of the drum 335, the second support part 503 supports the pipette tips 2 scooped up by the segmenting part 335*b* from below. The second support part 503 is formed to have a downward slope with respect to the opening 335*c*. Therefore, when the opening 335*c* and the opening 30*c* of the chassis 30*a* agree with each other by the rotation of the drum 335, the pipette tips 2 scooped up by the segmenting part 335*b* to be conveyed to the opening 30*c* of the chassis 30*a* slip down the second support part 503 downwardly sloped with respect to the opening 335*c*, and sent to the conveying path 34 described later through the opening 335*c* and the opening 30*c* of the chassis 30*a*. When the opening 335*c* and the opening 30*c* of the chassis 30*a* do not agree with each other, the opening 335*c* is covered by the chassis 30*a*, whereby the pipette tips 2 held by the segmenting part 335*b* are not sent out of the drum 335.

Figure 10:
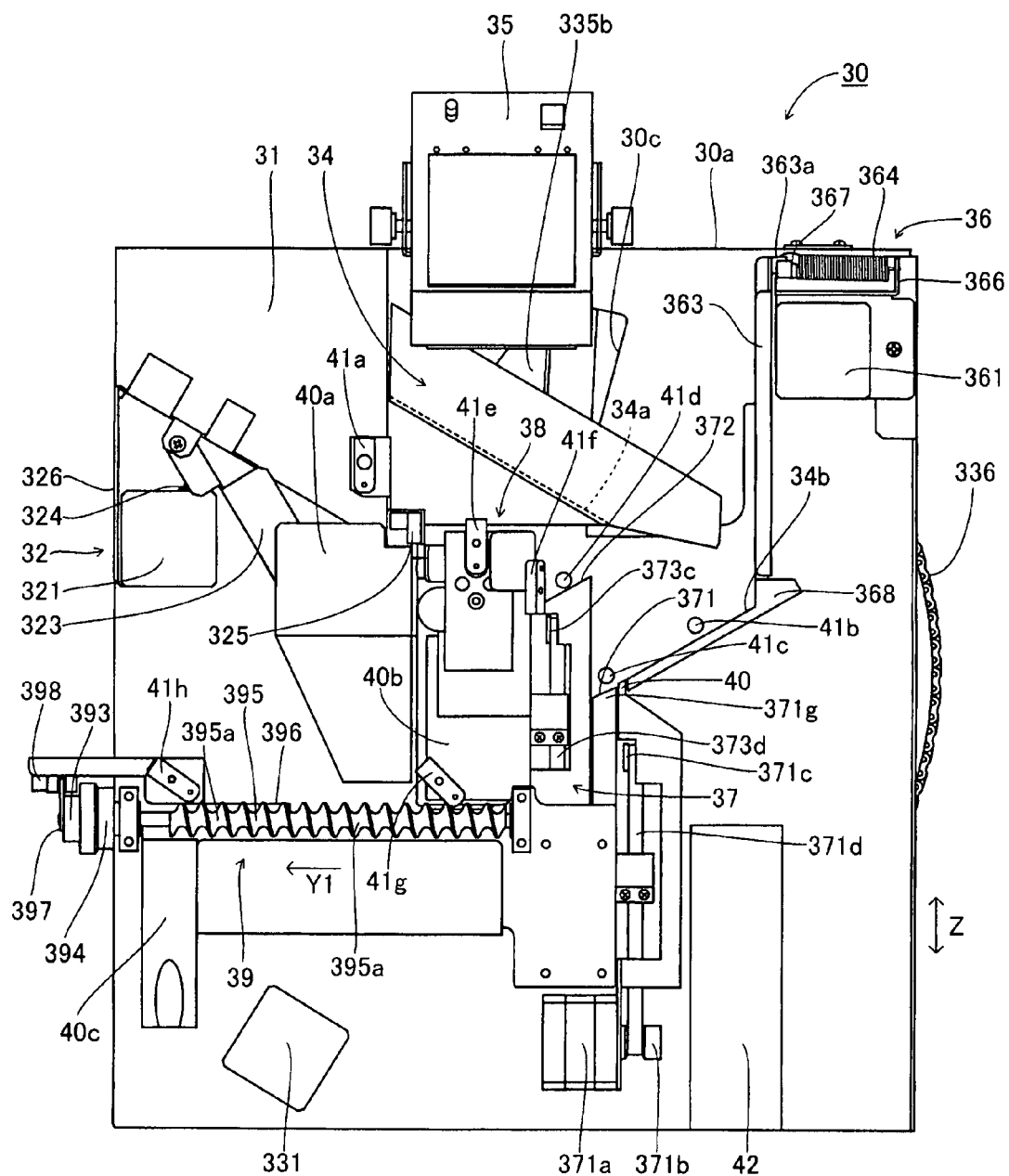
FIG. 10 is a front view of the automatic pipette tip supply device according to one embodiment shown in FIG. 5.

The conveying path 34 is composed of two inclined paths 34*a* and 34*b* for conveying the predetermined amount (five to fifteen in the present embodiment) of pipette tips 2 sent from the tip supply mechanism section 33 as shown in FIGS. 6 and 10. The inclined paths 34*a* and 34*b* of the conveying path 34 are provided in order to direct the pipette tips 2 sent from the segmenting part 335*b* at the drum 335 of the tip supply mechanism section 33 to the sort mechanism section 37, described later, by rolling down the pipette tips 2 sent from the segmenting part 335*b* of the tip supply mechanism section 33.

Figure 11:
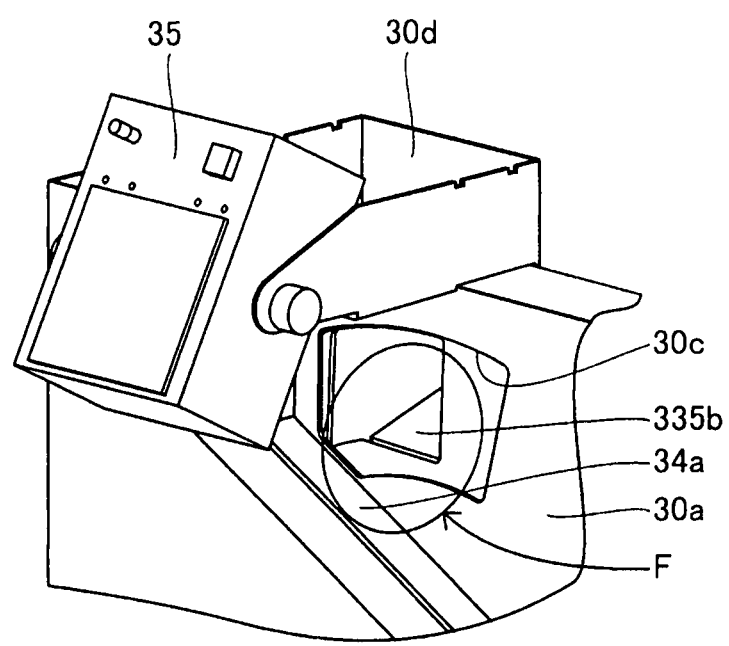
FIG. 11 is a perspective view showing a neutralizing fan of the automatic pipette tip supply device according to one embodiment shown in FIG. 5.

The neutralizing fan 35 has a function of sending ionizing air, and provided above the conveying path 34. There may be the case where static electric charges are produced on the pipette tips 2 caused by the pipette tips 2 accommodated in the drum 335 rubbing against each other due to the rotation of the drum 335. The neutralizing fan 35 can remove static electric charges on the pipette tips 2. The neutralizing fan 35 has a function of blowing ionized air, so that the static electricity charged at the pipette tips 2 can be removed. The neutralizing fan 35 is held so that both side surfaces are sandwiched at a holding part 30*d* having a horseshoe shape when seen in plan view arranged above the chassis 30*a*, as shown in FIGS. 5, 8, 10 and 11. The neutralizing fan 35 held at the holding part 30*d* of the chassis 30*a* is arranged so that the air blow port 35*a* faces the opening 30*c* of the chassis 30*a* and the portion (region F of FIG. 11) for receiving the pipette tip 2 of the inclined path 34*a* of the conveying path 34, as shown in FIGS. 8 and 11. In other words, the neutralizing fan 35 is arranged so as to blow the ionized air to the pipette tip 2 lifted by the segmenting part 335*b* of the drum 355 through the opening 30*c* of the chassis 30*a*, and to blow the ionized air to the pipette tip 2 sent from the segmenting part 335*b* and positioned at the inclined path 34*a* of the conveying path 34. Furthermore, the neutralizing fan 35 is controlled so as to be driven based on the rotating operation of the drum 35. That is, the neutralizing fan 35 is configured so as to be driven (turned ON) only while the pipette tips 2 are positioned in region F of FIG. 11 by being controlled so as to be driven (turned ON) only for a predetermined time from when the segmenting part 335*b* of the drum 335 is exposed through the opening 30*c* of the chassis 30*a*.

Figure 12:
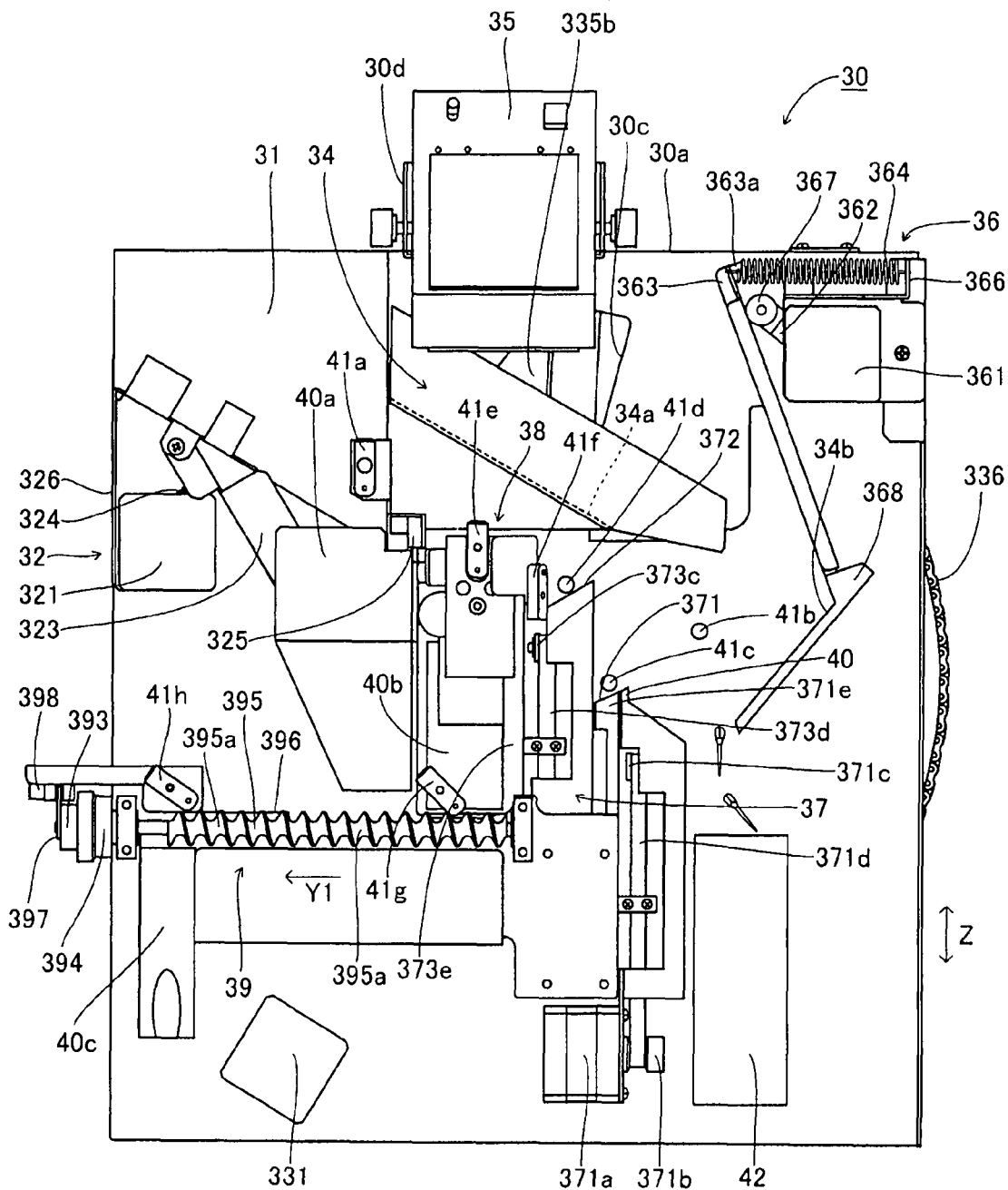
FIG. 12 is a front view showing a state in which a discharge mechanism section of the automatic pipette tip supply device according to one embodiment shown in FIG. 5 is located at a second position.
Figure 13:
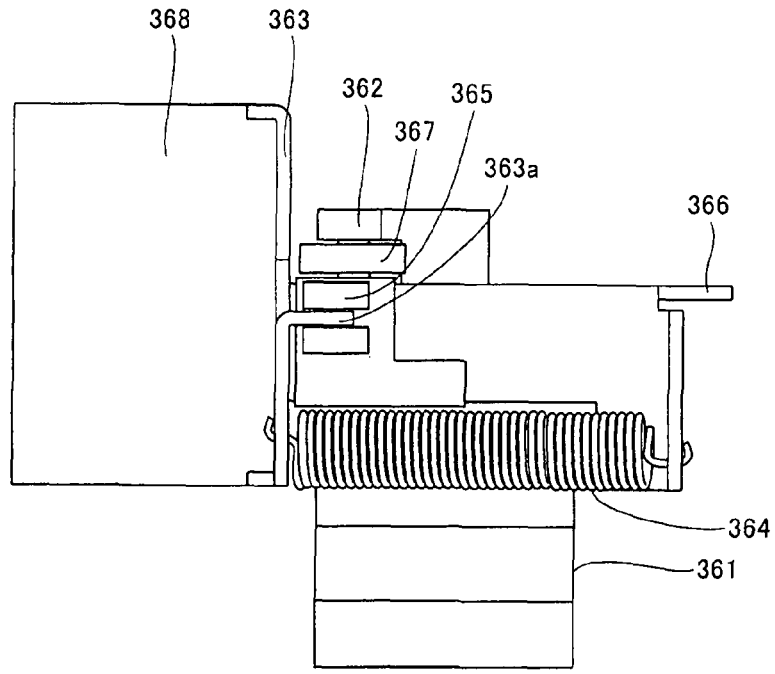
FIG. 13 is a plan view of a discharge mechanism section of the automatic pipette tip supply device according to one embodiment shown in FIG. 5.
Figure 14:
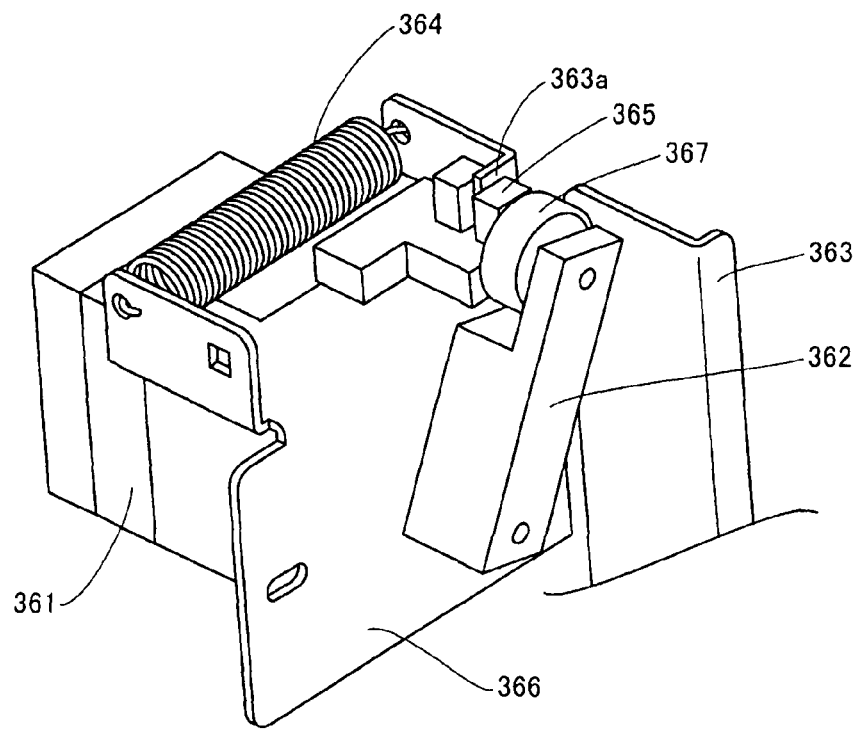
FIG. 14 is a perspective view of a discharge mechanism section of the automatic pipette tip supply device according to one embodiment shown in FIG. 5.
Figure 15:
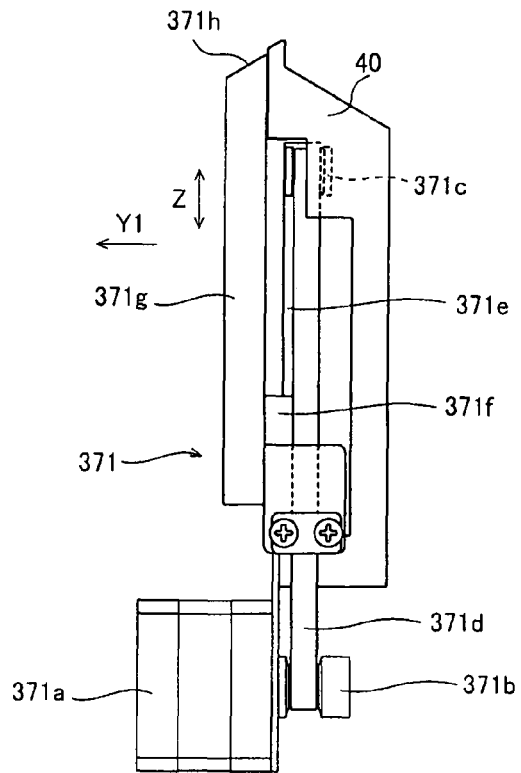
FIG. 15 is a front view of a cut-to-form mechanism section of the automatic pipette tip supply device according to one embodiment shown in FIG. 5.

The discharge mechanism section 36 has a function of discharging the stuck pipette tip 2 when the pipette tip 2 is stuck on a slanted surface part 368 of a later-described turning member 363 constituting the inclined path 34*b* of the conveying path 34 of the pipette tip 2. As shown in FIGS. 10 and 12, the discharge mechanism section 36 is configured so as to turn from a first position shown in FIG. 10 at where the pipette tips 2 can be conveyed to a second position (open position) shown in FIG. 12 at where the pipette tips 2 can be discharged. As shown in FIGS. 10, and 12 to 14, the discharge mechanism section 36 is configured by a motor 361 acting as a driving source, a pressing member 362 attached to the motor 361, a turning member 363 pressed against the pressing member 362, an extension coil spring 364, and a light shielding sensor 365. The motor 361 is attached to a steel plate 366 attached to the chassis 30*a*. One end of the extension coil spring 364 is attached to the steel plate 366, and the other end of the extension coil spring 364 is attached to the turning member 363. In other words, the extension coil spring 364 is arranged so as to bias the turning member 363 in a direction of moving away from the second position (see FIG. 12). A roller 367 for pressing the turning member 363 is attached to the pressing member 362. Further, the turning member 363 includes a resinous slanted surface part 368 that constitutes the inclined path 34*b* and has the slope substantially same as the slope of a slanted surface part 371*h* of a push-up plate 371*g* of a cut-to-form mechanism section 371 of the sort mechanism section 37, which will be described below, and the slope of an upper surface of a junction member 40 constituting the inclined path 34*b* when the turning member 363 turns to the position where the pipette tips 2 can be conveyed (see FIG. 10). The slanted surface part 368 has a function of rolling down the pipette tips 2 received from the inclined path 34*a* to the partition mechanism section 37 to be hereinafter described through a relay member 40 when turned to the first position, and discharging the pipette tips 2 stuck at the slanted surface part 368 when turned to the second position (open position). The light shielding sensor 365 is arranged so as to detect the detection strip 363*a* of the turning member 363 when the turning member 363 is turned to the first position.

As shown in FIGS. 5 and 10, a detection sensor (transmissive sensor) 41*b* is provided for detecting the presence of the pipette tip 2 on the slanted surface part 368 of the turning member 363 when the turning member 363 is turned to the position where the pipette tip 2 can be conveyed. Specifically, the detection sensor 41*b* can detect whether the pipette tip 2 is stuck or not on the slanted surface part 368 of the turning member 363.

In the present embodiment, the sort mechanism section 37 is provided for sorting one by one the pipette tips 2 received from the slanted surface part 368 of the turning member 363 and sending the sorted pipette tip 2 to a later-described movement section 38. As shown in FIGS. 6 and 10, the sort mechanism section 37 includes the cut-to-form mechanism section 371 that lifts up the pipette tips 2 received from the slanted surface part 368 through the junction member 40, a storage section 372 provided so as to be adjacent to the cut-to-form mechanism section 371, a cut-to-form mechanism section 373 that lifts up the pipette tip 2 received from the storage section 372, and a wall section 374 arranged so as to be adjacent to the cut-to-form mechanism section 373. The cut-to-form mechanism section 371, the storage section 372, the cut-to-form mechanism section 373, and the wall section 374 are arranged in the order of the cut-to-form mechanism section 371, storage section 372, cut-to-form mechanism section 373 and wall section 374 from the junction member 40 at the upstream side to the movement section 38 at the downstream side.

In the present embodiment, the cut-to-form mechanism section 371 has a function of supplying two to three pipette tips 2 to the later-described storage section 372 by lifting up the received pipette tips 2. The cut-to-form mechanism section 371 is composed of a stepping motor 371a acting as a driving source, a pulley 371b connected to the rotational axis of the stepping motor 371a, a pulley 371c arranged to have a predetermined space from the pulley 371b, a drive transmission belt 371d attached to the pulley 371b and pulley 371c, a linear moving guide composed of a slide rail 371e attached to the junction member 40 so as to extend in the vertical direction (Z direction) and a slide main body 371f movable along the slide rail 371e, and a push-up plate 371g coupled to the slide main body 371f. Thus, when the stepping motor 371a is driven, the drive transmission belt 371d is driven through the pulley 371b, so that the slide main body 371f coupled to the drive transmission belt 371d moves along the slide rail 371e to move the push-up plate 371g in the Z direction. Therefore, the pipette tip 2 placed onto the slanted surface part 371h of the push-up plate 371g are lifted up to be sent to the storage section 372. The slanted surface part 371h of the push-up plate 371g is a slope downward toward the storage section 372 (see FIG. 16) (in the direction shown by an arrow Y1).

Figure 16:
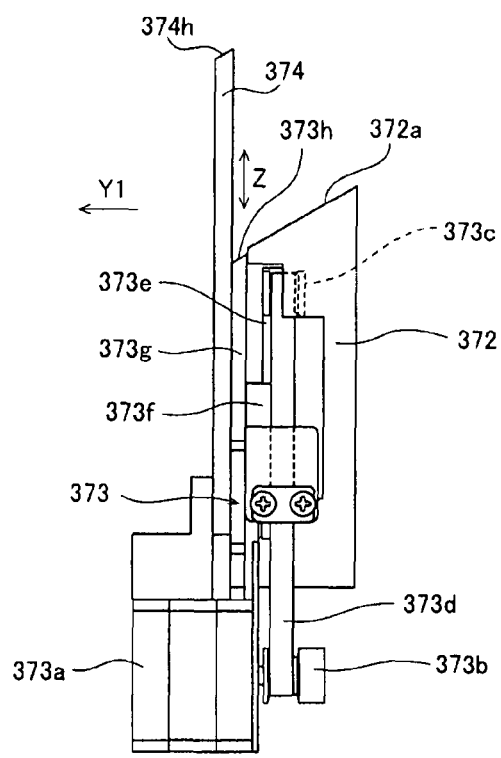
FIG. 16 is a front view of the cut-to-form mechanism section and a wall section of the automatic pipette tip supply device according to one embodiment shown in FIG. 5.

In the present embodiment, the storage section 372 has a function for storing the pipette tip 2 pushed up by the push-up plate 371g of the cut-to-form mechanism section 371 and for directing the pipette tip 2 to the cut-to-form mechanism section 373. As shown in FIG. 16, the storage section 372 includes a slanted surface part 372a that is a slope downward toward the cut-to-form mechanism section 373 from the cut-to-form mechanism section 371. The slanted surface part 372a slips down the pipette tip 2 pushed up by the push-up plate 371g in order to direct the pipette tip 2 to the later-described cut-to-form mechanism section 373.

Figure 17:
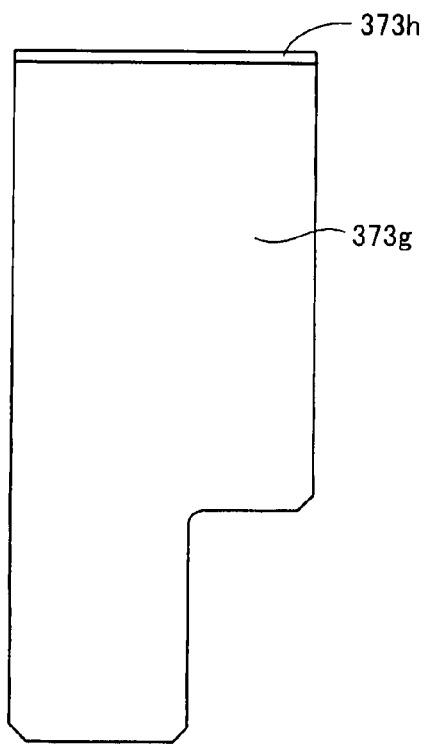
FIG. 17 is a front view of a push-up plate of the cut-to-form mechanism section shown in FIG. 15.
Figure 18:
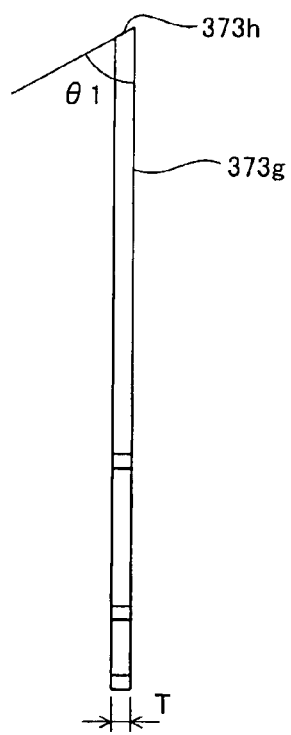
FIG. 18 is a side view of the push-up plate of the cut-to-form mechanism section shown in FIG. 15.

The cut-to-form mechanism section 373 has a function for sending one at a time the pipette tip 2 slipping down the slanted surface part 372a of the storage section 372 to the later-described wall section 374. The cut-to-form mechanism section 373 is composed of a stepping motor 373a acting as a driving source, a pulley 373b connected to the rotational axis of the stepping motor 373a, a pulley 373c arranged to have a predetermined space from the pulley 373b, a drive transmission belt 373d attached to the pulley 373b and pulley 373c, a linear moving guide composed of a slide rail 373e attached to the storage section 372 so as to extend in the vertical direction (Z direction) and a slide main body 373f movable along the slide rail 373e, and a push-up plate 373g coupled to the slide main body 373f. Thus, when the stepping motor 373a is driven, the drive transmission belt 373d is driven through the pulley 373b, so that the slide main body 373f coupled to the drive transmission belt 373d moves along the slide rail 373e to move the push-up plate 373g in the Z-direction. Therefore, the pipette tip 2 placed onto the slanted surface part 373h of the push-up plate 373g is lifted up to be sent to the wall section 374. In the present embodiment, the slanted surface part 373h of the push-up plate 373g is a slope downward toward the wall section 374 (in the direction shown by an arrow Y1) as shown in FIGS. 16 to 18, wherein its tilt angle θ1 (see FIG. 18) is about 60 degrees. The pipette tip 2 placed onto the slanted surface part 373h of the push-up plate 373g is lifted up by the push-up plate 373g while being supported by the wall section 374 so as not to slip down to the wall section 374.

In the present embodiment, the push-up plate 373g is designed so as to have a maximum of two pipette tips 2 placed onto the slanted surface part 373h. Specifically, as shown in FIG. 18, the push-up plate 373g has a thickness T (about 4.0 mm) that is smaller than the outer diameter R (about 7.0 mm) (see FIG. 2) of the attachment part 2c of the pipette tip 2. Therefore, there is no chance that the pipette tip 2 is arranged side by side on the slanted surface part 373h of the push-up plate 373g, whereby it can be prevented that two or more pipette tips 2 are placed onto the slanted surface part 373h except that the pipette tips 2 are overlapped vertically. Even when the pipette tips 2 are placed onto the push-up plate 373g as vertically overlapped, the push-up plate 373g in the present embodiment is designed such that one or both of two pipette tips 2 become unbalanced to thereby fall down to the storage section 372 from the slanted surface part 373h.

Figure 19:
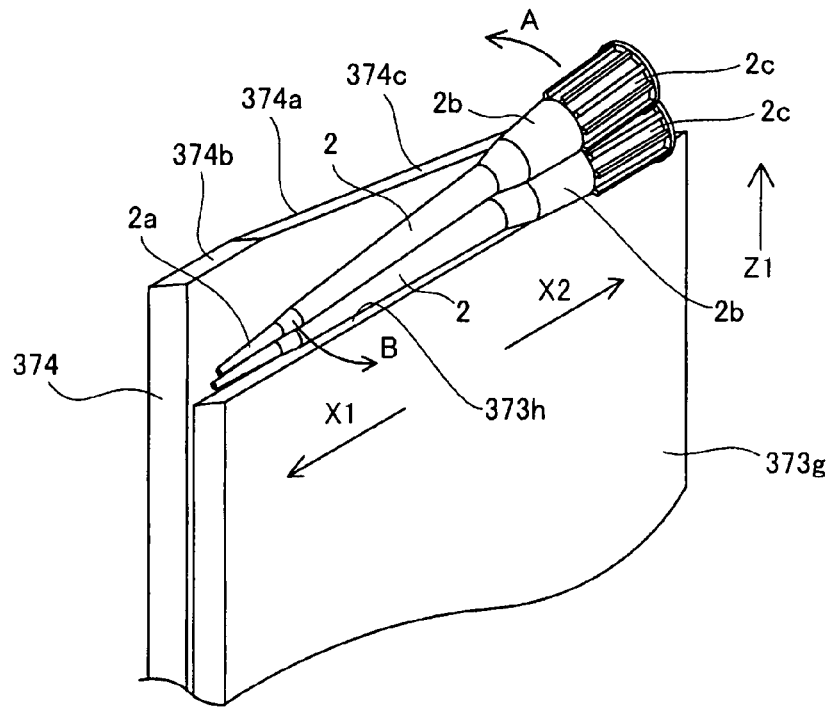
FIG. 19 is a perspective view showing a state in which the push-up plate of the cut-to-form mechanism section shown in FIG. 16 is located at a first stopping position.
Figure 20:
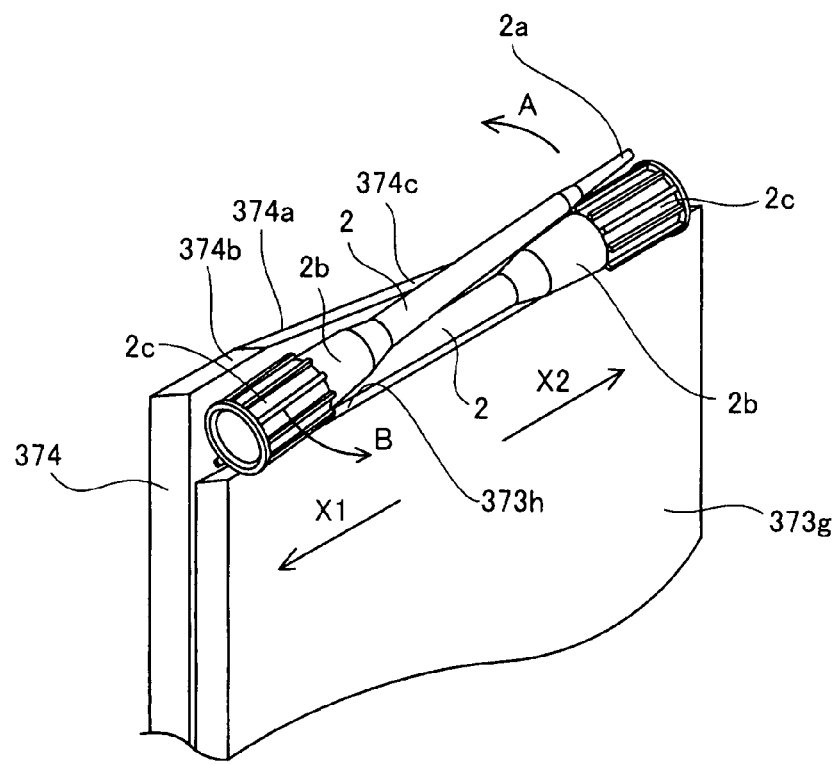
FIG. 20 is a perspective view showing a state in which the push-up plate of the cut-to-form mechanism section shown in FIG. 16 is located at a second stopping position.
Figure 21:
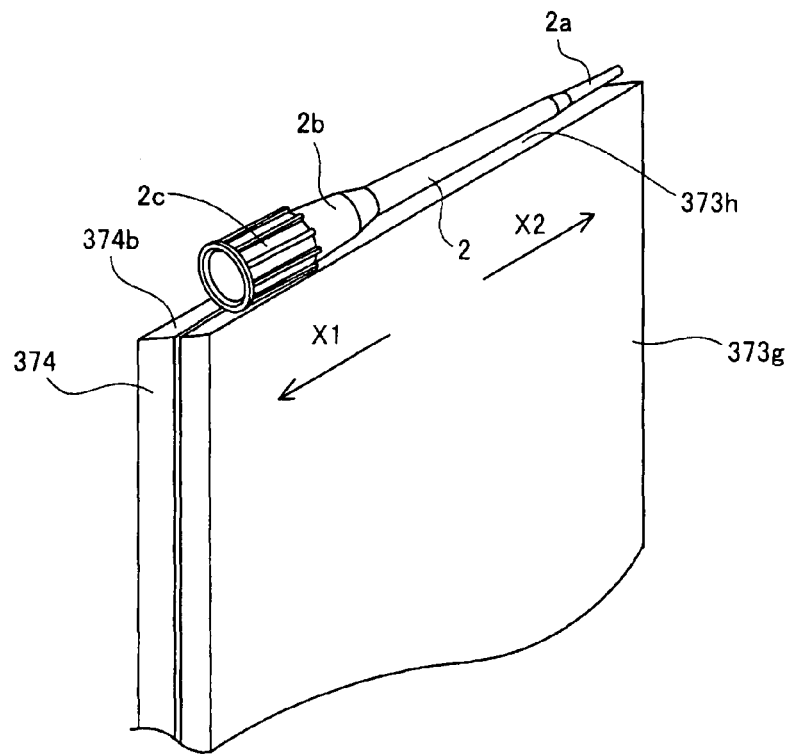
FIG. 21 is a perspective view showing a state in which the push-up plate of the cut-to-form mechanism section shown in FIG. 16 is located at a sending position.

In the present embodiment, the push-up plate 373g is configured to be movable in the vertical direction (Z direction) along the wall section 374 between the receiving position where the pipette tip 2 falling from the storage section 372 as described above is received and a sending position where the received pipette tip 2 is sent to the later-described wall section 374. Further, the push-up plate 373g is set so as to be capable of stopping at two predetermined portions (first stopping position and second stopping position) different from the receiving position and sending position. The receiving position is the position where the pipette tip 2 slipping down the slanted surface part 372a of the storage section 372 can be received as shown in FIG. 16. The first stopping position is the position where the upper pipette tip 2 slips down to the wall section 374, when two pipette tips 2 are vertically overlapped with each other with the attachment parts 2c facing in the direction shown by an arrow X2 as shown in FIG. 19. The second stopping position is the position where a part of the upper pipette tip 2 slips down to the wall section 374 when two pipette tips 2 are vertically overlapped with each other with each of them facing in the opposite direction as shown in FIG. 20. At the second stopping position, a part of an upper end portion 374a of the wall section 374 is positioned below a part of an upper end portion of the push-up plate 373g, and the other portion of the upper end portion of the wall section 374 is positioned above the other portion of the upper end portion of the first push-up plate 373g. The sending position is the position where one pipette tip 2 slips down to the wall section 374 as shown in FIG. 21. Accordingly, the push-up plate 373g can stop up to three times until it reaches the sending position shown in FIG. 21 from the receiving position shown in FIG. 16, including the case that it stops at the sending position. Further, since the push-up plate 373g is configured to move by the drive of the stepping motor 373a as shown in FIG. 16, it is possible to stop the push-up plate 373g at the accurate position according to the number of steps transmitted to the stepping motor 373a.

Figure 22:
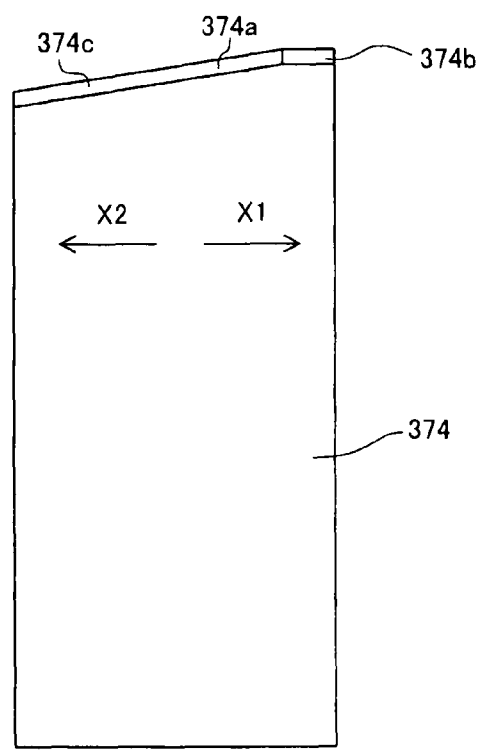
FIG. 22 is a front view of the wall section shown in FIG. 16.
Figure 23:
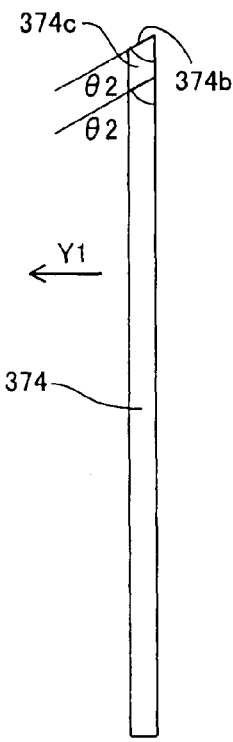
FIG. 23 is a side view of the wall section shown in FIG. 16.
Figure 25:
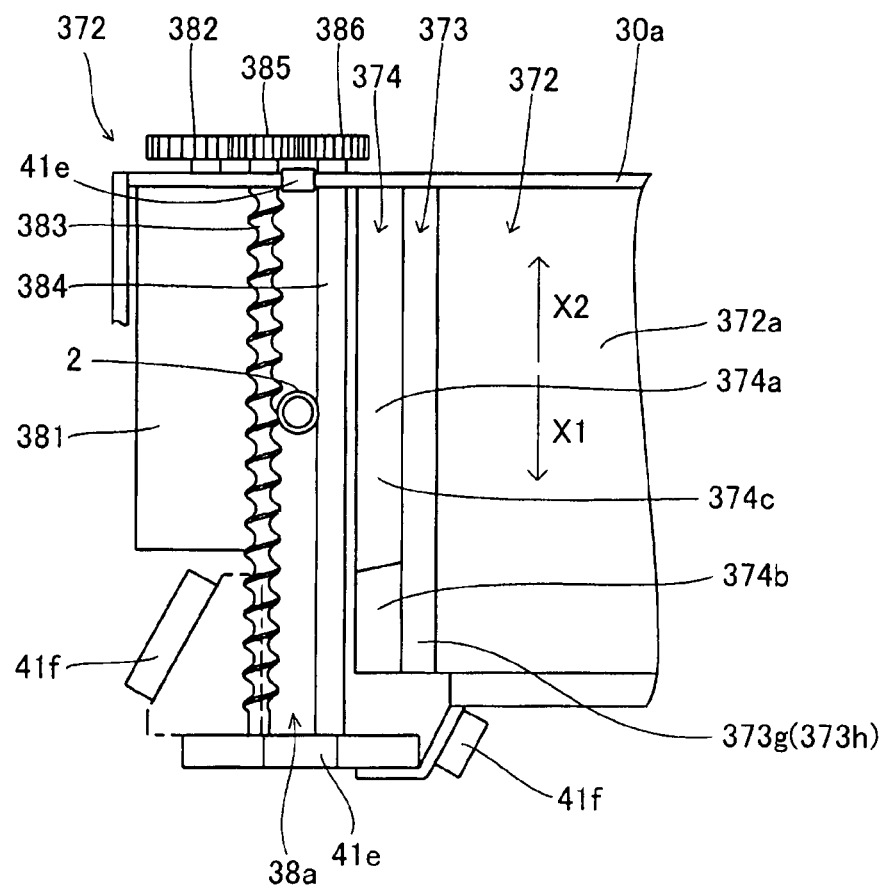
FIG. 25 is a plan view of a movement section of the automatic pipette tip supply device according to one embodiment shown in FIG. 5.

In the present embodiment, the wall section 374 has a function for supplying the pipette tip 2 lifted up by the push-up plate 373g of the cut-to-form mechanism section 373 to the movement section 38 (see FIG. 25). As shown in FIGS. 16, 22 and 23, the upper end portion 374a of the wall section 374 has a slanted surface part 374b and slanted surface part 374c that are inclined downward toward the movement section 38 with a tilt angle θ2 (about 60 degrees), like the slanted surface part 373h of the push-up plate 373g. Thus, it is possible to slip down the pipette tip 2 lifted up by the push-up plate 373g to the movement section 38, whereby the pipette tip 2 can easily be guided to the movement section 38.

Figure 24:
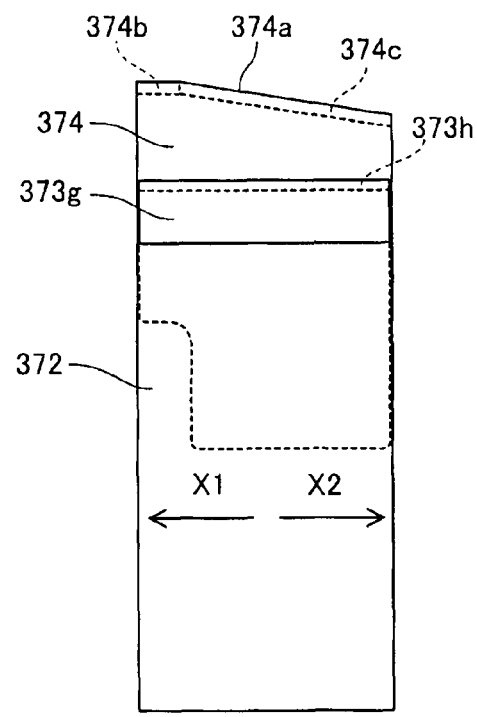
FIG. 24 is a front view of a storage section, push-up plate and wall section of the cut-to-form mechanism section of the automatic pipette tip supply device according to one embodiment shown in FIG. 5.

In the present embodiment, the slanted surface part 374c of the upper end portion 374a of the wall section 374 is formed so as to be inclined along the widthwise direction of the push-up plate 373g as shown in FIG. 24, wherein the slanted surface part 374c inclines downward in the direction of the arrow X2. Therefore, when the push-up plate 373g of the cut-to-form mechanism section 373 is at the receiving position, the upper end portion 374a of the wall section 374 is positioned above the slanted surface part 373h of the push-up plate 373g as shown in FIG. 16. When the push-up plate 373g is at the first stopping position (see FIG. 19), second stopping position (see FIG. 20) and sending position (see FIG. 21), at least a part of the upper end portion 374a of the wall section 374 is positioned below the pipette tip 2 placed onto the slanted surface part 373h of the push-up plate 373g. When the push-up plate 373g is at the sending position, the slanted surface part 374b of the upper end portion 374a is arranged so as to be on the same plane as the slanted surface part 373h of the push-up plate 373g as shown in FIG. 21.

As shown in FIGS. 5 and 10, the detection sensor (transmissive sensor) 41c is provided for detecting the presence of the pipette tip 2 placed onto the slanted surface part 371h of the push-up plate 371g when the push-up plate 371g of the cut-to-form mechanism section 371 is located at the receiving position. This detection sensor (transmissive sensor) 41c is provided at the position spaced from the detection sensor (transmissive sensor) 41b at a predetermined space.

A detection sensor (transmissive sensor) 41d is provided for detecting the presence of the pipette tip 2 placed onto the slanted surface part 372a of the storage section 372. When the detection sensor (transmissive sensor) 41d detects the pipette tip 2, the cut-to-form mechanism section 371 is controlled not to be operated. Specifically, when there is no pipette tip 2 stored in the storage section 372, the push-up plate 371g of the cut-to-form mechanism section 371 is operated to replenish the storage section 372 with the pipette tip 2 in the present embodiment.

Figure 26:
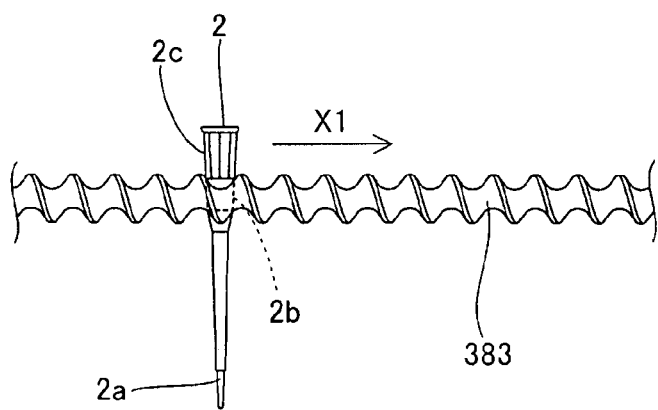
FIG. 26 is a side view of the movement section of the automatic pipette tip supply device according to one embodiment shown in FIG. 5.
Figure 27:
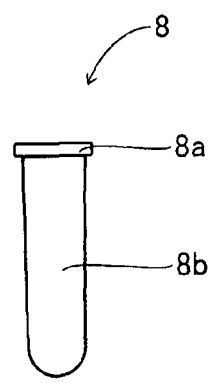
FIG. 27 is a front view of a cuvette used for the immune analyzing device shown in FIG. 1.

The movement section 38 is provided for moving the pipette tip 2 slipping down from the wall section 374 of the sort mechanism section 37 in the direction of an arrow X1 (see FIG. 25). The movement section 38 is composed of a motor 381 acting as a driving source, a gear 382 attached to the motor 381, a feed screw 383, a shaft 384, a gear 385 attached to the feed screw 383 and meshed with the gear 382, and a gear 386 attached to the shaft 384 and meshed with the gear 385, as shown in FIG. 25. The feed screw 383 and the shaft 384 are rotatably mounted to the chassis 30a. The feed screw 383 and the shaft 384 are arranged parallel to each other with a space substantially same as the outer diameter of the body part 2b (see FIG. 2) of the pipette tip 2. Thus, the feed screw 383 and the shaft 384 can support the body part 2b of the pipette tip 2. In this case, since the body part 2b of the pipette tip 2 supported by the feed screw 383 and the shaft 384 is positioned above the center of gravity G (see FIG. 2) of the pipette tip 2, the pipette tip 2 is supported by the feed screw 383 and the shaft 384 with the distal end 2a of the pipette tip 2, slipping down from the wall section 374 of the sort mechanism section 37, facing downward, as shown in FIG. 26. A throwing part 38a having a space greater than the outer diameter R (see FIG. 2) of the attachment part 2c of the pipette tip 2, when seen in plan view, is provided at the feed screw 383 and the shaft 384 in the direction of the arrow X1.

In the present embodiment, a detection sensor (transmissive sensor) 41e is provided for detecting the presence of the pipette tip 2 supported by the feed screw 383 and the shaft 384 as shown in FIG. 25. When the detection sensor (transmissive sensor) 41e detects the pipette tip 2, the push-up plate 373g of the cut-to-form mechanism section 373 is controlled not to move upward. Specifically, in the present embodiment, when there is no pipette tip 2 supported by the feed screw 383 and the shaft 384, the push-up plate 373g of the cut-to-form mechanism section 373 is moved upward to replenish the pipette tip 2 to the wall section 374. When the detection sensor 41e detects the pipette tip 2, the push-up plate 373g moving upward is immediately stopped, and moved downward.

A detection sensor (transmissive sensor) 41f is provided for detecting whether or not the pipette tip 2 conveyed by the feed screw 383 and the shaft 384 is sent to the throwing section 38a.

The shoot 40b is arranged to lead the pipette tip 2 (see FIG. 2) dropped from the input part 38a (see FIG. 25) of the movement section 38 to the movement section 39.

The movement section 39 is provided for moving the pipette tip 2 guided from the movement section 38, which moves the pipette tip 2 in the direction of the arrow X1, through the shoot 40b in the direction of the arrow Y1. As shown in FIGS. 5, 6 and 10, the movement section 39 is composed of a motor 391 acting as a driving source, a pulley 392 connected to the rotational axis of the motor 391, a pulley 393 arranged to have a predetermined space from the pulley 392, a drive transmission belt 394 mounted to the pulley 392 and pulley 393, a feed screw 395 mounted so as to be rotatable with the rotation of the pulley 393, a wall section 396 attached to the chassis 30a, a detection strip 397 attached to the pulley 393, and a light shielding sensor 398. The feed screw 395 has a groove part 395a having a width smaller than the outer diameter R of the attachment part 2c (see FIG. 2) of the pipette tip 2 and greater than the outer diameter of the body part 2b (see FIG. 2) of the pipette tip 2. The wall section 396 is arranged parallel to the feed screw 395 with a predetermined space so as to prevent the pipette tip 2 fitted into the groove part 395a of the feed screw 395 from falling off. The light shielding sensor 398 is arranged so as to detect the detection strip 397 attached to the pulley 393 when the pulley 393 that rotates the feed screw 395 rotates.

The detection sensor (transmissive sensor) 41g is arranged to detect whether or not the pipette tip 2 led from the movement section 38 by way of the shoot 40b has reached to the movement section 39, as shown in FIGS. 5 and 6. The detection sensor (transmissive sensor) 41h is arranged to detect whether or not the pipette tip 2 conveyed by the movement section 39 has been conveyed up to immediately before being dropped to the shoot 40c to be hereinafter described.

The shoot 40c is arranged to lead the pipette tip 2 conveyed by the movement section 39 to the tip installing part 23b of the conveying rack 23 of the emergency specimen and tip conveying section 20. The shoot 40c is formed so that the distal end 2a of the pipette tip 2 passing therethrough slides down The tip collecting container 42 is arranged at a position capable of collecting the pipette tips 2 discharged by the discharge mechanism section 36.

Figure 28:
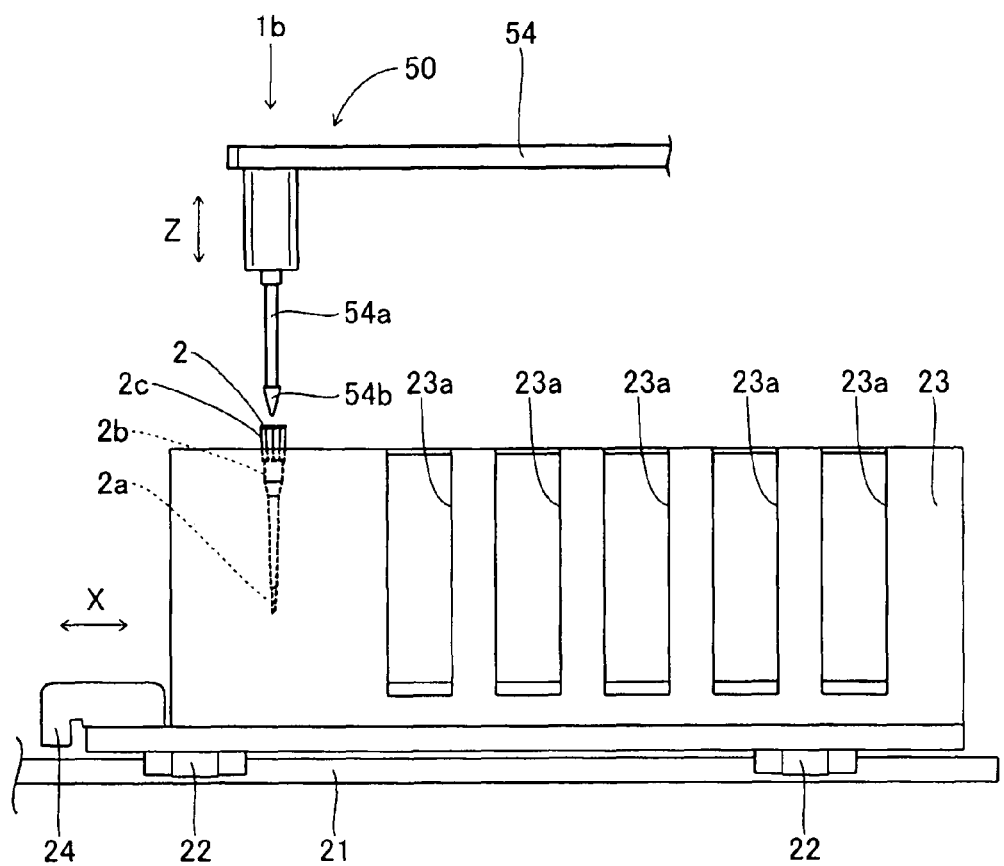
FIG. 28 is a side view of an emergency specimen and tip conveying section and specimen dispensing arm of the immune analyzing device shown in FIG. 1.

The specimen dispensing arm 50 has a function of dispensing the specimen in the test tube 3 conveyed to the suction position 1a (see FIG. 1) by the specimen conveying section 10 or the specimen in the test tube 3 conveyed to the attachment position 1b (see FIG. 1) by the emergency specimen and tip conveying section 20 to the cuvette 8 (see FIG. 27) held at the holding portion 81b of the rotating table part 81a of the primary reaction section 81 to be hereinafter described. The specimen dispensing arm 50 includes a motor 51, a drive transmitting section 52 connected to the motor 51, and an arm part 54 attached to the drive transmitting section 52 by way of a shaft 53, as shown in FIGS. 1 and 28. The drive transmitting section 52 is configured to turn the arm part 54 with the shaft 53 as the center and move the same in the up and down direction (Z direction) by the driving force from the motor 51. A nozzle portion 54a for suctioning and discharging the specimen is arranged at the distal end of the arm part 54. The pipette tip 2 conveyed by the conveying rack 23 of the emergency specimen and tip conveying section 20 is attached to the distal end 54b of the nozzle portion 54a.

Figure 29:
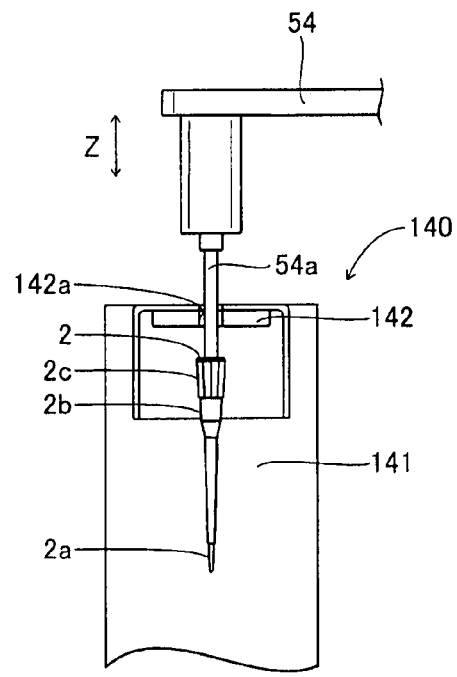
FIG. 29 is a side view for explaining the releasing operation of the pipette tip attached to the specimen dispensing arm of the immune analyzing device shown in FIG. 1.

The tip releasing section 140 (see FIG. 1) is arranged to release the pipette tip 2 attached to the specimen dispensing arm 50. The tip releasing section 140 includes a steel plate 141 arranged so as to extend in the vertical direction (Z direction), and a release strip 142 made of resin attached to the steel plate 141, as shown in FIG. 29. A cut-out part 142a having a diameter smaller than the diameter of the attachment part 2c (see FIG. 31) of the pipette tip 2 and greater than the diameter of the distal end 54b (see FIG. 31) of the arm part 54 of the specimen dispensing arm 50 is formed in the release strip 142.

A reagent installing section 61 (see FIG. 1) includes an installing part 61a for installing the reagent bin 5 accommodating the R1 reagent containing trapped antibody and the reagent bin 7 accommodating the R3 reagent containing labeled antibody, an upper surface part 61b arranged at the upper part of the installing part 61a so that foreign materials such as dust do not enter the R1 reagent in the reagent bin 5 or the R3 reagent in the reagent bin 7 installed in the installing part 61a, and a lid part 61c attached to the upper surface part 61b in an openable and closable manner. A groove part 61d to be inserted with a nozzle 91e of the reagent dispensing arm 91 to be hereinafter described, and a groove part 61e to be inserted with a nozzle 93e of the reagent dispensing arm 93 are formed in the upper surface part 61b. The installing part 61a is rotatably configured so as to convey the installed reagent bin 5 and the reagent bin 7 to the position corresponding to the groove part 61d and the groove part 61e of the upper surface part 61b.

The reagent installing section 62 (see FIG. 1) includes an installing part 62a for installing a reagent bin 6 accommodating the R2 reagent containing magnetic particles, an upper surface part 62b arranged at the upper part of the installing part 62a so that foreign materials such as dust do not enter the R2 reagent in the reagent bin 6 installed in the installing part 62a, and a lid part 62c attached to the upper surface part 62b in an openable and closable manner. A groove part 62d to be inserted with a nozzle 92e of the reagent dispensing arm 92 to be hereinafter described is formed in the upper surface part 62b. The installing part 62a is rotatably configured so as to convey the installed reagent bin 6 to a position corresponding to the groove part 62d.

A cuvette supply section 70 (see FIG. 1) is configured so as to be able to sequentially supply a plurality of cuvettes 8 (see FIG. 27) to a holding portion 81b of the rotating table part 81a of the primary reaction section 81. The cuvette supply section 70 includes a hopper 71 capable of accommodating the plurality of cuvettes 8, two guiding plates 72 arranged below the hopper 71, a supporting table 73 arranged at the lower end of the guiding plate 72, and a supply catcher part 74. The two guiding plates 72 are arranged parallel to each other at a distance smaller than the diameter of a collar part 8a (see FIG. 27) of the cuvette 8 and larger than the diameter of a core 8b (see FIG. 27) of the cuvette 8. The plurality of cuvettes 8 supplied to the hopper 71 are arrayed along the guiding plate 72 with the collar part 8a engaging the upper surface of the two guiding plates 72 by applying vibration to the hopper 71.

The supporting table 73 includes a rotating part 73a arranged rotatable with respect to the supporting table 73, and a concave part 73b arranged so as to be adjacent to the rotating part 73a. Three cut-outs 73c are formed on the outer peripheral portion of the rotating part 73a at every predetermined angle (120° in the present embodiment). The cut-out 73c is arranged to accommodate the cuvette 8 guided by the guiding plate 72 one by one. The concave part 73b is configured so as to receive the cuvette 8 that rotates in a state accommodated in the cut-out 73c of the rotating part 73a.

The supply catcher part 74 (see FIG. 1) has a function of moving the cuvette 8 received by the concave part 73b to the holding portion 81b of the rotating table part 81a of the primary reaction section 81. The supply catcher part 74 includes a motor 74a, a pulley 74b connected to the motor 74a, a pulley 74c arranged at a predetermined distance from the pulley 74b, a drive transmission belt 74d attached to the pulley 74b and the pulley 74c, an arm part 74e attached to the pulley 74c by way of a shaft, and a driving part 74f for moving the arm part 74e in the up and down direction (Z direction). A chuck part 74g for sandwiching and gripping the cuvette 8 is arranged at the distal end of the arm part 74e.

The primary reaction section 81 (see FIG. 1) is arranged to rotatably move the cuvette 8 held by the holding portion 81b of the rotating table part 81a over a predetermined angle at every predetermined period (18 seconds in the present embodiment), and to stir the specimen, R1 reagent and the R2 reagent in the cuvette 8. The primary reaction section 81 is configured by a rotating table part 81a for conveying the cuvette 8 accommodating the specimen, the R1 reagent, and the R2 reagent in the rotating direction, and a conveying mechanism part 81c for stirring the specimen, the R1 reagent and the R2 reagent in the cuvette 8 and conveying the cuvette 8 accommodating the stirred specimen, the R1 reagent and the R2 reagent to the BF separating section 101 to be hereinafter described.

The reagent dispensing arm 91 (see FIG. 1) has a function of suctioning the R1 reagent in the reagent bin 5 installed in the installing part 61a of the reagent installing section 61 and dispensing the suctioned R1 reagent to the cuvette 8 dispensed with the specimen of the holding portion 81b of the rotating table part 81a of the primary reaction section 81. The reagent dispensing arm 91 includes a motor 91a, a drive transmission part 91b connected to the motor 91a, and an arm part 91d attached to the drive transmission part 91b by way of a shaft 91c. The drive transmission part 91b is configured to turn the arm part 91d with the shaft 91c as the center and move the same in the up and down direction (Z direction) by the driving force from the motor 91a. The nozzle 91e for suctioning and discharging the R1 reagent in the reagent bin 5 is attached to the distal end of the arm part 91d. That is, the nozzle 91 suctions the R1 reagent in the reagent bin 5 through the groove part 61d of the upper surface part 91e of the reagent installing section 61, and thereafter the suctioned R1 reagent is dispensed into the cuvette 8 dispensed with the specimen.

The reagent dispensing arm 92 (see FIG. 1) has a function of dispensing the R2 reagent in the reagent bin 6 installed in the installing part 62a of the reagent installing section 62 into the cuvette 8 dispensed with the specimen and the R1 reagent of the primary reaction section 81. The reagent dispensing arm 92 includes a motor 92a, a drive transmission part 92b connected to the motor 92a, and an arm part 92d attached to the drive transmission part 92b by way of a shaft 92c. The drive transmission part 92b is configured so as to turn the arm part 92d with the shaft 92c as the center and move the same in the up and down direction (Z direction) by the driving force from the motor 92a. A nozzle 92e for suctioning and discharging the R2 reagent in the reagent bin 6 is attached to the distal end of the arm part 92d. Therefore, the nozzle 92e suctions the R2 reagent in the reagent bin 6 by way of the groove part 62d of the upper surface part 62b of the reagent installing section 62, and thereafter the suctioned R2 reagent is dispensed into the cuvette 8 dispensed with the specimen and the R1 reagent.

The BF (Bound Free) separating section 101 (see FIG. 1) is arranged to remove the non-reacting R1 reagent in the cuvette 8 (see FIG. 27) received from the conveying mechanism part 81c of the primary reaction section 81. The BF separating section 101 includes an installing part 101a for installing the cuvette 8 and conveying the same in the rotating direction, and a separation stirring part 101b for suctioning the non-reacting R1 reagent. The installing part 101a includes three installation holes 101c for holding the cuvette 8, and a magnet 101d arranged lateral to each of the three installation holes 101a. Thus, the bound antigen, trapped antibody and magnetic particles in the cuvette 8 installed in the installation hole 101c can be attracted to the magnet 101d side. Furthermore, the non-reacting (free) R1 reagent not binding with the magnetic particles can be removed by suctioning the specimen and the like in the cuvette 8 in the attracted state by means of the separation stirring part 101b.

A conveyor catcher section 110 (see FIG. 1) has a function of conveying the cuvette 8 (see FIG. 27) of the installing part 101a of the BF separating section 101 in which the non-reacting R1 reagent etc. is separated to the holding portion 82b of the rotating table part 82a of the secondary reaction section 82. The conveying catcher section 110 includes a motor 110a, a pulley 110b connected to the motor 110a, a pulley 110c arranged at a predetermined distance from the pulley 110b, a drive transmission belt 110d attached to the pulley 110b and the pulley 110c, an arm part 110e attached to the pulley 110c by way of a shaft, and a driving part 110f for moving the arm part 110e in the up and down direction (Z direction). A chuck part 110g for sandwiching and gripping the cuvette 8 is arranged at the distal end of the arm part 110e.

The secondary reaction section 82 (see FIG. 1) has a configuration similar to the primary reaction section 81, and is arranged to rotatably move the cuvette 8 held at the holding portion 82b of the rotating table part 82a over a predetermined angle at every predetermined period (18 seconds in the present embodiment), and stir the specimen, R1 reagent, R2 reagent, R3 reagent and R5 reagent in the cuvette 8. The secondary reaction section 82 is configured by a rotating table part 82a for conveying the cuvette 8 accommodating the specimen, R1 reagent, R2 reagent, R3 reagent and R5 reagent in the rotating direction, and a conveying mechanism part 82c for stirring the specimen, R1 reagent, R2 reagent, R3 reagent, and R5 reagent in the cuvette 8 and conveying the cuvette 8 accommodating the stirred specimen and the like to the conveying to the BF separating section 102 to be hereinafter described. Furthermore, the conveying mechanism part 82c has a function of conveying the cuvette 8 processed by the BF separating section 102 again to the holding portion 82b of the rotating table part 82a.

The reagent dispensing arm 93 (see FIG. 1) has a function of suctioning the R3 reagent in the reagent bin 7 installed in the installing part 61a of the reagent installing section 61 and dispensing the suctioned R3 reagent into the cuvette 8 dispensed with the specimen, R1 reagent, and R2 reagent of the secondary reaction section 82. The reagent dispensing arm 93 includes a motor 93a, a drive transmission part 93b connected to the motor 93a, and an arm part 93d attached to the drive transmission part 93b by way of a shaft 93c. The drive transmission part 93b is configured so as to turn the arm part 93d with the shaft 93c as the center and move the same in the up and down direction (Z direction) by the driving force from the motor 93a. A nozzle 93e for suctioning and discharging the R3 reagent in the reagent bin 7 is attached to the distal end of the arm part 93d. That is, the nozzle 93e suctions the R3 reagent in the reagent bin 7 through the groove part 61e of the upper surface part 61b of the reagent installing section 61, and thereafter, the suctioned R3 reagent is dispensed into the cuvette 8 dispensed with the specimen, R1 reagent, and R2 reagent.

The BF separating section 102 (see FIG. 1) has a configuration similar to the BF separating section 101, and is arranged to remove the non-reacting R3 reagent in the cuvette 8 (see FIG. 27) received from the conveying mechanism part 82c of the secondary reaction section 82. The BF separating section 102 includes an installing part 102a for installing the cuvette 8 and for conveying the same in the rotating direction, and a separation stirring part 102b for suctioning the non-reacting R3 reagent. The installing part 102a includes three installation holes 102c for holding the cuvette 8, and a magnet 102d arranged lateral to each of the three installation holes 101a. Thus, the bound magnetic particles, antigen, and labeled antibody in the cuvette 8 installed in the installation hole 102c can be attracted to the magnet 102d side. Furthermore, the non-reacting (free) R3 reagent can be removed by suctioning the specimen and the like in the cuvette 8 in the above attracted state by means of the separation stirring part 102b.

The reagent dispensing arm 94 (see FIG. 1) has a function of dispensing the R5 reagent containing light emitting substrates in a reagent bin (not shown) installed at the lower part of the immune analyzing device 1 into the cuvette 8 accommodating the specimen, R1 reagent, and R2 reagent, and R3 reagent of the secondary reaction section 82. The reagent dispensing arm 94 includes a motor 94a, a drive transmission part 94b connected to the motor 94a, and an arm part 94d attached to the drive transmission part 94b by way of a shaft. The drive transmission part 94b is configured so as to turn the arm part 94d with the shaft as the center and move the same in the up and down direction (Z direction) by the driving force from the motor 94a. A nozzle (not shown) for suctioning and discharging the R5 reagent is attached to the distal end of the arm part 94c.

The detecting section 120 (see FIG. 1) is arranged to acquire the light produced in the reaction process of the labeled antibody that binds with the antigen of the specimen performed with a predetermined process and the light emitting substrate by means of a photo multiplier tube to measure the amount of antigen contained in the relevant specimen. The detecting section 120 is configured by an installing part 121 for installing the cuvette 8 accommodating the specimen, R1 reagent, R2 reagent, R3 reagent, and R5 reagent, and a conveying mechanism part 122 for conveying the cuvette 8 (see FIG. 27) held at the holding portion 82b of the rotating table part 82a of the secondary reaction section 82.

The disposing section 130 (see FIG. 1) is arranged to dispose the measured specimen etc. measured by the detecting section 120, and the cuvette 8 (see FIG. 27) accommodating the relevant specimen etc. The disposing section 130 is configured by a suction part 131 for suctioning the specimen and various regents in the cuvette 8, and a disposing hole 132 arranged at a position at a predetermined distance from the suction part 131. Thus, the suction part 131 suctions the measured specimen etc., and thereafter the used cuvette 8 is disposed into a dust box (not shown) arranged at the lower part of the immune analyzing device 1 through the disposing hole 132.

The tip releasing section 140 (see FIG. 1) is arranged to release the pipette tip 2 attached to the specimen dispensing arm 50. The tip releasing section 140 includes a steel plate 141 arranged so as to extend in the vertical direction (Z direction), and a release strip 142 made of resin attached to the steel plate 141, as shown in FIG. 29. A cut-out part 142*a* having a diameter smaller than the diameter R of the attachment part 2*c* (see FIG. 2) of the pipette tip 2 and greater than the diameter of the distal end 54*b* (see FIG. 28) of the specimen dispensing arm 50 is formed in the release strip 142.

In the present embodiment, the control section 150 (see FIG. 1) has a function of controlling various operations by the pipette tip supply device 30. Specifically, the control section 150 receives signals detected by the detection sensors 41*a* to 41*h* in order to control the operations of the motors provided at the corresponding part, such as the stepping motor 331 of the tip supply mechanism section 33, or stepping motors 371*a* and 373*a* of the sort mechanism section 37. When the detection sensor 41*d* (see FIGS. 6 and 10) detects the pipette tip 2 on the slanted surface part 372*a* (see FIG. 16) of the storage section 372, the control section 150 stops the operation of the stepping motor 371*a* (see FIG. 15) of the cut-to-form mechanism section 371 so as to control the push-up plate 371*g* not to move upward. In the present embodiment, when the detection sensor 41*e* (see FIGS. 6, 10 and 25) detects the pipette tip 2 supported by the feed screw 383 and the shaft 384, the control section 150 stops the operation of the stepping motor 373*a* (see FIG. 16) of the cut-to-form mechanism section 373 and drives the stepping motor 373*a* in the reverse direction so as to control the push-up plate 373*g* (see FIG. 16) to move downward.

FIGS. 29, and 32 to 37 are views for explaining the operation for supplying the pipette tip to the specimen dispensing arm of the pipette tip supply device according to the embodiment shown in FIG. 5. Subsequently, the operation for supplying the pipette tip to the specimen dispensing arm of the pipette tip supply device will be explained with reference to FIGS. 1 to 12, 15, 16, 18 to 20, 24 to 29, and 30 to 35.

As shown in FIG. 5, an operator casually inputs plural pipette tips 2 (see FIG. 2) taken out of a bag to the input port 31*a* of the tip refill section 31 of the pipette tip supply device 30. In this case, the turning member 323 of the turning mechanism section 32 turns to the position covering the discharge port 31*b* of the tip refill section 31, whereby plural pipette tips 2 are stored in the tip refill section 31. In this case, the pipette tips 2 in the tip refill section 31 are detected by the detection sensor (transmissive sensor) 41*a*.

When the detection sensor (transmissive sensor) 41*i* of the drum 335 does not detect the pipette tip 2 in the drum 335, the turning member 323 of the turning mechanism section 32 is turned to the position where the discharge port 31*b* of the tip refill section 31 is open, whereby a predetermined amount of pipette tips 2 are thrown into the drum 335 of the tip supply mechanism section 33 from the discharge port 31*b* of the tip refill section 31 through the shoot 40*a* and the opening 30*b* (see FIG. 8) of the chassis 30*a*.

When the detection sensor (transmissive sensor) 41*b* shown in FIGS. 5 and 10 does not detect the pipette tip 2 on the slanted surface part 368 of the discharge mechanism section 36, the drum part 333 of the tip supply mechanism section 33 is rotated, whereby a predetermined amount (five to fifteen in the present embodiment) of the pipette tip 2 is sent to the conveying path 34 by the segmenting part 335*b*. On the other hand, when the detection sensor 41*b* detects the pipette tip 2 on the slanted surface part 368 of the discharge mechanism section 36, the drum part 333 of the tip supply mechanism section 33 is not rotated, so that the pipette tip 2 is not supplied to the conveying path 34.

In the present embodiment, it is configured such that the light shielding sensor 334 detects the detection strip 337 when the opening 335*c* and the opening 30*c* of the chassis 30*a* agree with each other. When the light shielding sensor 334 detects the detection strip 337, the drum 335 is controlled so as to temporarily stop its rotation. Therefore, this can secure the time taken for all of the pipette tips 2 held by the segmenting part 335*b* to slip down from the second support member 503 and send to the outside of the drum 334. Further, the segmenting part 335*b* has a size and shape of having the number of pipette tips 2 to be sent to the conveying path 34 to be of a predetermined number (five to fifteen in the present embodiment). Accordingly, pipette tips 2 in an excess amount are not sent to the sort mechanism section 37 through the conveying path 34, thereby being difficult to cause stuck pipette tips 2. Moreover, each of the drum 335 and the tip refill section 31 has the size capable of accommodating about 500 pipette tips 2, which means that the drum 335 and the tip refill section 31 can accommodate a great number of pipette tips 2 in one replenishment. Therefore, if a great number of pipette tips 2 are replenished to the drum 335 and the tip refill section 31 at one time, a predetermined amount of pipette tips 2 can continuously be sent from the drum 335 without the need for a user to replenish the pipette tips 2 again and again. Since excessive pipette tips 2 are not sent to the conveying path 34, the pipette tip 2 is thoroughly exposed to the ionized air sent from the neutralizing fan 35, whereby the neutralization is effectively performed.

In the present embodiment, the pipette tip 2 sent to the conveying path 34 by the segmenting part 335*b* of the drum 335 at the tip supply mechanism section 33 falls down the inclined path 34*a* of the conveying path 34 while static electric charges are removed by the ionized air sent from the neutralizing fan 35 as shown in FIG. 11. Since the pipette tip 2 falling down the inclined path 34*a* is exposed to the ionized air sent from the neutralizing fan 35 in this case, the pipette tip 2 is thoroughly exposed to the ionized air, thereby achieving effective neutralization. According to the experiment carried out by the present inventors, it was found that the voltage of the pipette tip 2 charged with static electric charges having voltage of several kilovolts was lowered to several volts.

As shown in FIGS. 8 and 9, a predetermined amount of pipette tips 2 are thrown to the drum 335 of the tip supply mechanism section 33 from the discharge port 31*b* of the tip refill section 31 through the shoot 40*a* and the opening 30*b* of the chassis 30*a* by turning the turning member 323 (see FIGS. 5 to 7) of the turning mechanism section 32 to the position where the discharge port 31*b* of the tip refill section 31 is open.

When the detection sensor (transmissive sensor) 41*b* shown in FIGS. 5 and 10 does not detect the pipette tip 2 on the slanted surface part 368 of the turning member 363 at the discharge mechanism section 36, the drum part 333 of the tip supply mechanism section 33 is rotated, whereby a predetermined amount (five to fifteen in the present embodiment) of the pipette tips 2 are sent to the conveying path 34 by the segmenting part 335*b*. On the other hand, when the detection sensor 41*b* detects the pipette tip 2 on the slanted surface part 368 of the turning member 363 at the discharge mechanism section 36, the drum part 333 at the tip supply mechanism section 33 is not rotated, so that the pipette tip 2 is not supplied to the conveying path 34.

The pipette tip 2 sent to the conveying path 34 by the segmenting part 335*b* of the drum 335 at the tip supply mechanism section 33 slips down the inclined path 34*a* of the conveying path 34, while static electric charges are removed by the ionized air sent from the neutralizing fan 35 as shown in FIG. 11. Thereafter, as shown in FIG. 6, the pipette tip 2 slipping down from the inclined path 34a of the conveying path 34 slips down the slanted surface part 368, constituting the inclined path 34b of the conveying path 34, of the turning member 363 at the discharge mechanism section 36 to be guided to the cut-to-form mechanism section 371 of the sort mechanism section 37. In this case, the detection sensor (transmissive sensor) 41b detects the presence of the pipette tip 2 on the slanted surface part 368 of the turning member 363, and the detection sensor (transmissive sensor) 41c detects the presence of the pipette tip 2 on the push-up plate 371g of the cut-to-form mechanism section 371.

When the detection sensors 41b and 41c detect the pipette tip 2 even if the push-up plate 371g of the cut-to-form mechanism section 371 is moved in the vertical direction predetermined number of times (e.g., fifteen times), it is determined that the pipette tip 2 is stuck on the slanted surface part 368 of the turning member 363 at the discharge mechanism section 36. Therefore, as shown in FIG. 12, the turning member 363 of the discharge mechanism section 36 is turned to the second position (open position). Thus, the pipette tip 2 stuck on the slanted surface part 368 of the turning member 363 is dropped down and collected by the tip collecting container 42.

Thereafter, the push-up plate 371g (see FIG. 15) of the cut-to-form mechanism section 371 at the sort mechanism section 37 is moved in the vertical direction (Z direction), whereby the pipette tip 2 placed onto the slanted surface part 371h of the push-up plate 371g is lifted up, and two to three pipette tips 2, the number of which is limited, are sent to the storage section 372 (see FIG. 16). In this case, the detection sensor (transmissive sensor) 41d (see FIG. 6) detects the presence of the pipette tip 2 on the slanted surface part 372a of the storage section 372. When the detection sensor 41d detects the pipette tip 2 on the slanted surface part 372a, the operation of the cut-to-form mechanism section 371 is stopped to discontinue the sending of the pipette tip 2 from the cut-to-form mechanism section 371 to the storage section 372. Two to three pipette tips 2 lifted up by the push-up plate 371g of the cut-to-form mechanism section 371 to the storage section 372 fall down the slanted surface part 372a of the storage section 372 to be guided to the cut-to-form mechanism section 373.

Then, the push-up plate 373g of the cut-to-form mechanism section 373 is moved upward (in the Z1 direction) from the receiving position to the sending position, whereby the pipette tip 2 placed onto the slanted surface part 373h of the push-up plate 373g at the cut-to-form mechanism section 373 is lifted up to send one pipette tip 2 to the wall section 374.

The sorting operation of the cut-to-form mechanism section 373 for supplying one by one the pipette tip 2 to the movement section 38 will be explained in detail.

Since the push-up plate 373g of the cut-to-form mechanism section 373 is, as shown in FIG. 18, designed to have a thickness T (about 4.0 mm) smaller than the outer diameter R (about 7.0 mm) of the attachment part 2c of the pipette tip 2 as described above, there is no chance that two or more pipette tips 2 are placed onto the slanted surface part 373h so long as the pipette tips 2 are vertically overlapped. In the present embodiment, even if the pipette tips 2 on the slanted surface part 373h are vertically overlapped, it is possible to prevent two pipette tips 2 from being supplied to the wall section 374.

Figure 32:
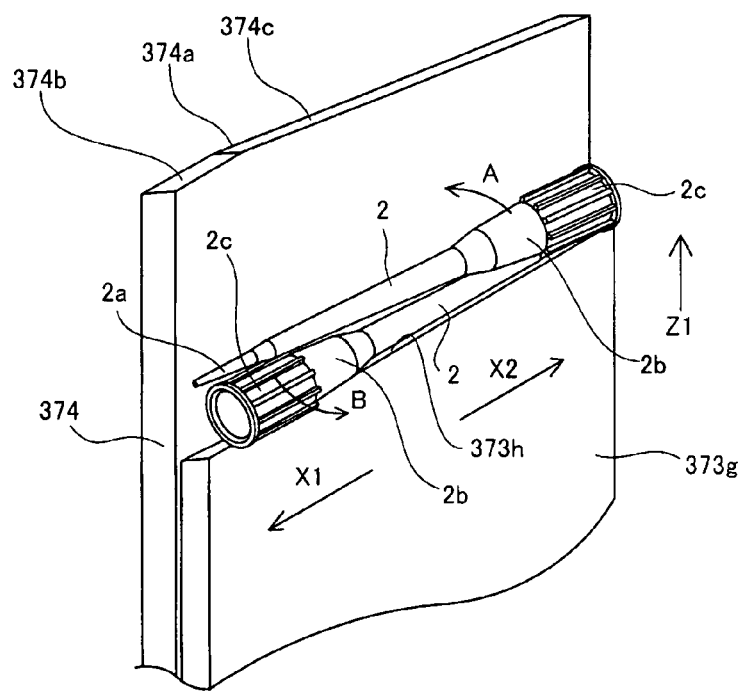
FIG. 32 is a perspective view for explaining a sorting operation of a sort mechanism section of the automatic pipette tip supply device according to one embodiment shown in FIG. 5.

When two pipette tips 2 are arranged so as to direct in the opposite direction as shown in FIG. 32, there may be the case in which two pipette tips 2 are placed onto the slanted surface part 373h of the push-up plate 373g as vertically overlapped.

Figure 33:
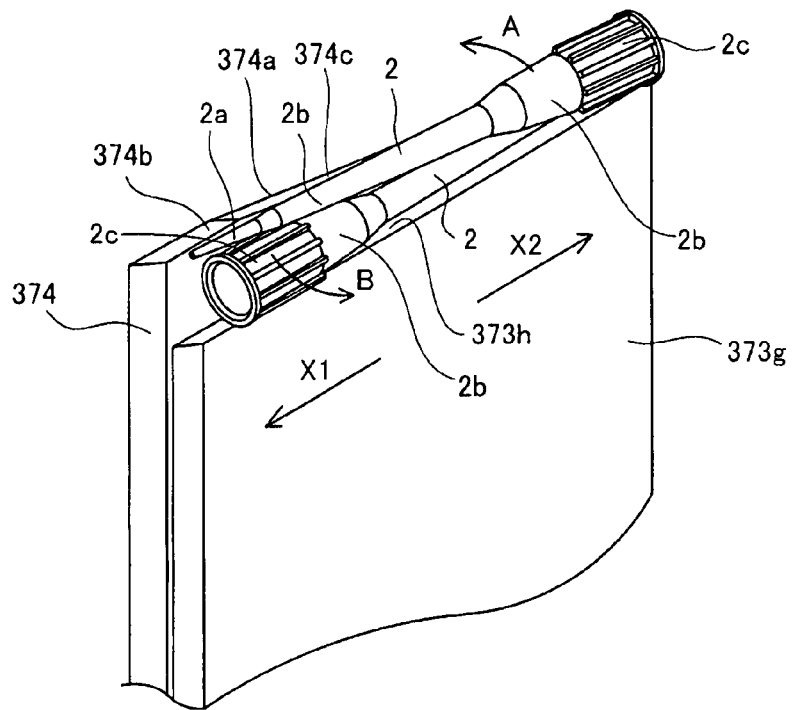
FIG. 33 is a perspective view for explaining a sorting operation of a sort mechanism section of the automatic pipette tip supply device according to one embodiment shown in FIG. 5.

FIG. 32 shows that the upper pipette tip 2 is arranged such that its attachment part 2c directs in the arrow X2 direction, while the lower pipette tip 2 is arranged such that its attachment part 2c directs in the arrow X1 direction. By driving the stepping motor 373a (see FIG. 16) of the cut-to-form mechanism section 373, the push-up plate 373g positioned at the receiving position and having placed thereon two pipette tips 2 moves in the arrow Z1 direction (upward) to stop at the first stopping position (see FIG. 19), and then, moves in the arrow Z1 direction (upward) until it stops at the second stopping position as shown in FIG. 33. In this case, the upper pipette tip 2 on the slanted surface part 373h that is inclined downward toward the wall section 374 is about to slip down to the wall section 374 from the slanted surface part 373h of the push-up plate 373g. Since the slanted surface part 374c of the wall section 374 is inclined downward toward the arrow X2 direction, the upper pipette tip 2 is about to slip down to the wall section 374 from the attachment part 2c in the arrow X2 direction, whereby the attachment part 2c turns in the arrow A direction and the distal end 2a turns in the arrow B direction. Thus, the attachment part 2c at the side where the position of center of gravity G is offset moves to the wall section 374, whereby the upper pipette tip 2 slips down the wall section 374.

Since the distal end 2a turns in the arrow B direction with the turning of the attachment part 2c of the upper pipette tip 2 in the arrow A direction, the attachment part 2c of the lower pipette tip 2 is pressed against the turning distal end 2a of the upper pipette tip 2, whereby the lower pipette tip 2 falls down to the storage section 372. Even if the lower pipette tip 2 does not fall down to the storage section 372, the detection sensor 41e detects the arrival of the upper pipette tip 2 to the movement section 38, so that it is possible to stop the upward movement of the push-up plate 373g. Thus, even if two pipette tips 2 are arranged in the opposite direction, one pipette tip 2 can be supplied to the wall section 374.

Figure 34:
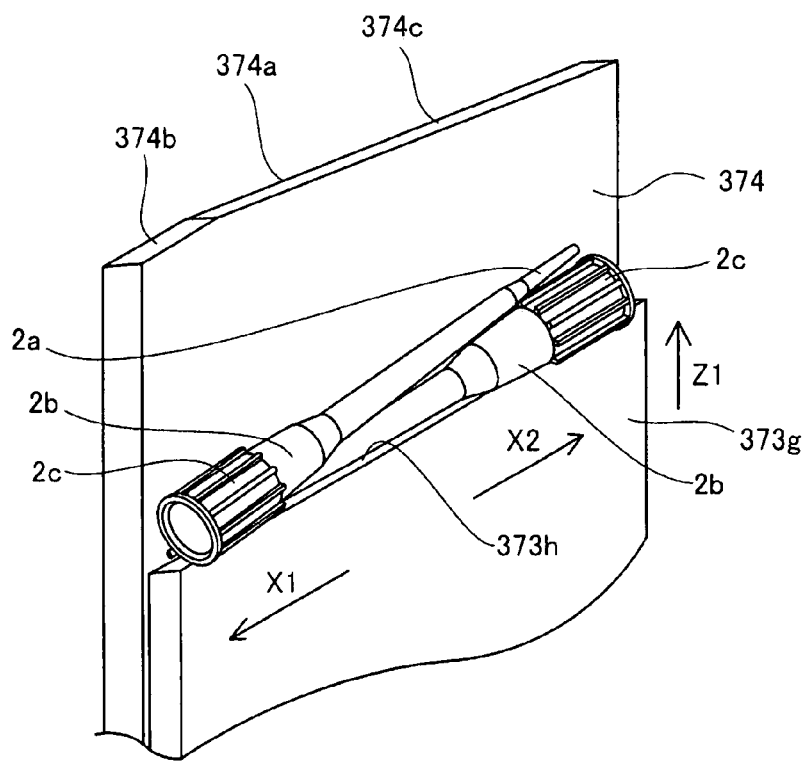
FIG. 34 is a perspective view for explaining a sorting operation of a sort mechanism section of the automatic pipette tip supply device according to one embodiment shown in FIG. 5.
Figure 35:
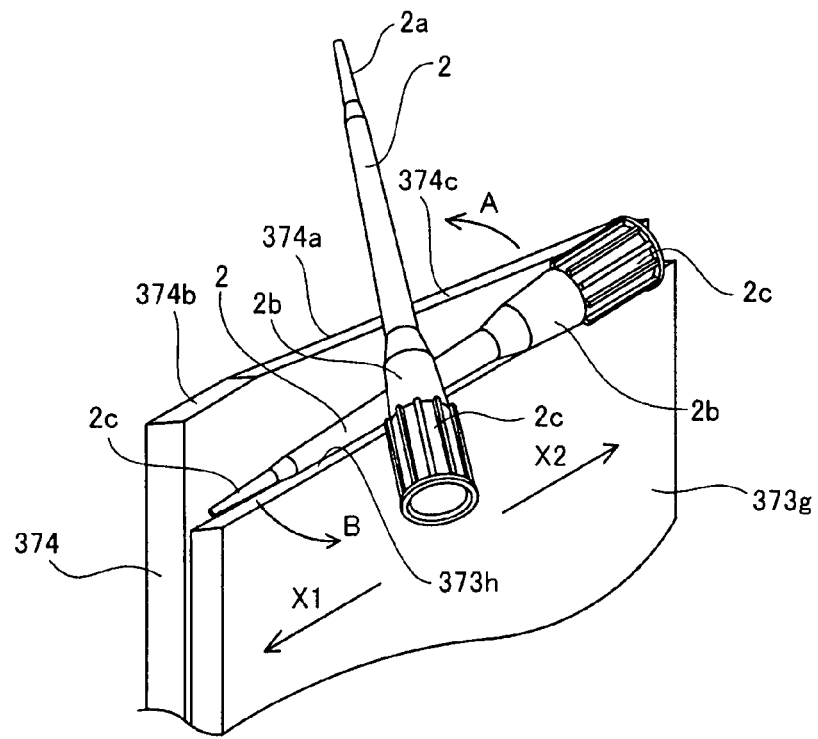
FIG. 35 is a perspective view for explaining a sorting operation of a sort mechanism section of the automatic pipette tip supply device according to one embodiment shown in FIG. 5.
Figure 36:
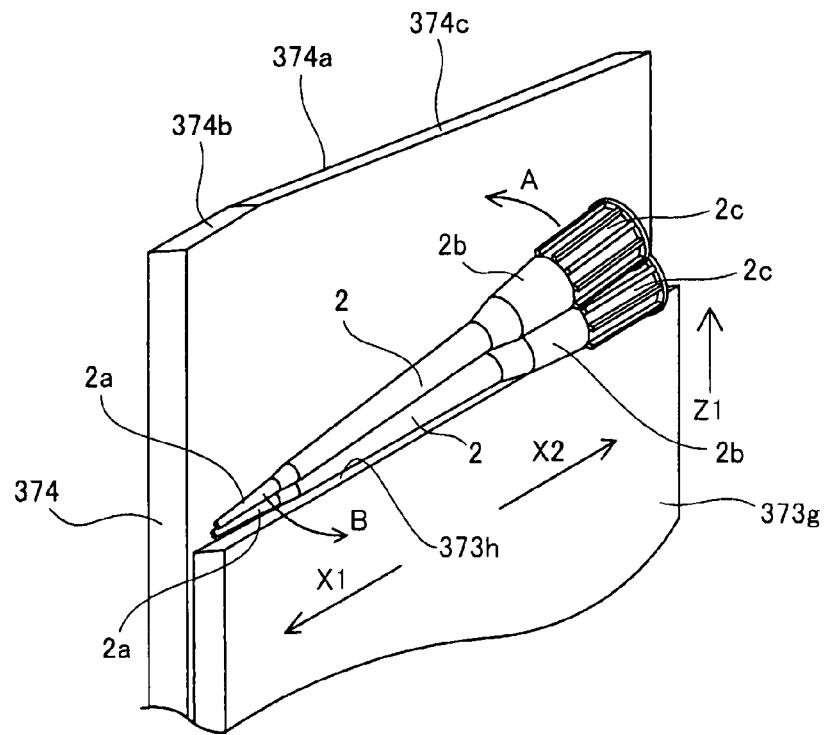
FIG. 36 is a perspective view for explaining a sorting operation of a sort mechanism section of the automatic pipette tip supply device according to one embodiment shown in FIG. 5.

Subsequently explained is the case in which the upper pipette tip 2 is arranged such that the attachment part 2c thereof directs in the arrow X1 direction and the lower pipette tip 2 is arranged such that the attachment part 2c thereof directs in the arrow X2 direction as shown in FIG. 34, different from the case shown in FIGS. 32 and 33 in which the upper pipette tip 2 is arranged such that the attachment part 2c thereof directs in the arrow X2 direction and the lower pipette tip 2 is arranged such that the attachment part 2c thereof directs in the arrow X1 direction. By driving the stepping motor 373a (see FIG. 16) of the cut-to-form mechanism section 373, the push-up plate 373g located at the receiving position and having placed thereon two pipette tips 2 moves in the arrow Z1 direction (upward) to stop at the first stopping position (see FIG. 19), and then, moves in the arrow Z1 direction (upward) until it stops at the second stopping position as shown in FIG. 20. In this case, the upper pipette tip 2 on the slanted surface part 373h that is inclined downward toward the wall section 374 is about to slip down to the wall section 374 from the slanted surface part 373h of the push-up plate 373g. Since the slanted surface part 374c of the wall section 374 is inclined downward toward the arrow X2 direction, the upper pipette tip 2 is about to slip down to the wall section 374 from the distal end 2a in the arrow X2 direction, whereby the distal end 2a turns in the arrow A direction and the attachment part 2c turns in the arrow B direction. Thus, as shown in FIG. 35, the attachment part 2c at the side where the position of center of gravity G is offset moves to the storage section 372, whereby the upper pipette tip 2 falls down to the storage section 372. Thereafter, the push-up plate 373g having placed thereon one pipette tip 2 that is the lower pipette tip 2 moves in the arrow Z1 direction until it reaches the sending position as shown in FIG. 36. Thus, one pipette tip 2 placed onto the slanted surface part 373h of the push-up plate 373g slips down the wall section 374 to be supplied to the movement section 38.

Figure 37:
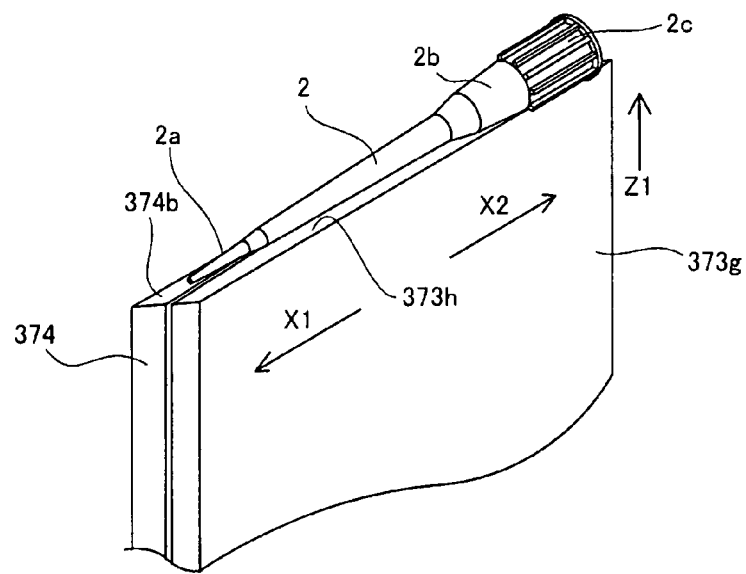
FIG. 37 is a perspective view for explaining a sorting operation of a sort mechanism section of the automatic pipette tip supply device according to one embodiment shown in FIG. 5.

Subsequently explained is the case in which the upper and lower pipette tips 2 are arranged such that the attachment parts 2c of both of them direct in the arrow X2 direction as shown in FIG. 37. By driving the stepping motor 373a (see FIG. 16) of the cut-to-form mechanism section 373, the push-up plate 373g located at the receiving position and having placed thereon two pipette tips 2 moves in the arrow Z1 direction (upward) to stop at the first stopping position, and then, moves in the arrow Z1 direction (upward) as shown in FIG. 19. In this case, the upper pipette tip 2 on the slanted surface part 373h that is inclined downward toward the wall section 374 is about to slip down to the wall section 374 from the slanted surface part 373h of the push-up plate 373g. Since the slanted surface part 374c of the wall section 374 is inclined downward toward the arrow X2 direction, the upper pipette tip 2 is about to slip down to the wall section 374 from the attachment part 2c in the arrow X2 direction, whereby the attachment part 2c turns in the arrow A direction and the distal end 2a turns in the arrow B direction. Thus, the attachment part 2c at the side where the position of center of gravity G is offset moves to the wall section 374, whereby the upper pipette tip 2 slips down the wall section 374.

In this case, the detection sensor 41e detects the arrival of the upper pipette tip 2 to the movement section 38, so that it is possible to stop the upward movement of the push-up plate 373g on which the lower pipette tip 2 is placed. Thus, even if two pipette tips 2 are arranged such that the attachment parts 2c of both of them direct in the arrow X2 direction, one pipette tip 2 can be supplied to the wall section 374.

As shown in FIG. 26, one pipette tip 2 slipping down from the wall section 374 of the sort mechanism section 37 has the body part 2b (see FIG. 2), which is above the position of center of gravity G, supported by the feed screw 383 and the shaft 384, whereby the distal end 2a of the pipette tip 2 is directed downward.

In this case, the detection sensor (transmissive sensor) 41e shown in FIGS. 5 and 26 detects the presence of the pipette tip 2 supported by the feed screw 383 and the shaft 384. Specifically, when the detection sensor 41e does not detect the pipette tip 2 supported by the feed screw 383 and the shaft 384, the cut-to-form mechanism section 371 and the cut-to-form mechanism section 373 of the sort mechanism section 37 are moved in the vertical direction (Z direction) in order to send one pipette tip 2 from the cut-to-form mechanism section 373 to the movement section 38 through the wall section 374 as shown in FIG. 6. On the other hand, when the detection sensor 41e detects the pipette tip 2 supported by the feed screw 383 and the shaft 384, the movement of the cut-to-form mechanism section 371 and the movement of the cut-to-form mechanism section 373 of the sort mechanism section 37 in the vertical direction (Z direction) are stopped to discontinue the supply of the pipette tip 2 to the movement section 38.

The pipette tip 2 held by the feed screw 383 and the shaft 384 is conveyed to the input part 38a (see FIG. 25) of the movement section 38 by rotating the feed screw 383 and the shaft 384 of the movement section 38. In this case, whether or not the pipette tip 2 sent by the feed screw 383 and the shaft 384 has been conveyed to the input part 38a is detected by the detection sensor (transmissive sensor) 41f, as shown in FIG. 25.

As shown in FIG. 6, the pipette tip 2 dropped from the input part 38a of the movement section 38 passes through the shoot 40b and reaches the movement section 39. In this case, whether or not the pipette tip 2 has reached the movement section 39 is detected by the detection sensor (transmissive sensor) 41g. Specifically, if the detection sensor 41g detects the pipette tip 2, the operation of the movement section 38 is stopped, thereby stopping the pipette tip 2 from being sent from the movement section 38 to the movement section 39. On the other hand, if the detection sensor 41g does not detect the pipette tip 2, the pipette tip 2 is supplied from the movement section 38 to the movement section 39 by rotating the feed screw 383 and the shaft 384 of the movement section 38.

The pipette tip 2 held one by one at the groove part 395a and the wall part 396 of the feed screw 395 is sequentially conveyed to the shoot 40c by rotating the feed screw 395 of the movement section 39. In this case, the detection sensor (transmissive sensor) 41h detects the presence of the pipette tip 2 at the position immediately before the shoot 40c. Specifically, the pipette tip 2 is rapidly conveyed to the position immediately before the shoot 40c by rotating the feed screw 395 until the detection sensor 41h detects the pipette tip 2 at the position immediately before the shoot 40c.

As shown in FIGS. 3 and 4, the pipette tip 2 sequentially conveyed one at a time by the movement section 39 passes through the shoot 40c and installed at the tip installing part 23b of the conveying rack 23 of the emergency specimen and tip conveying section 20. In this case, the emergency specimen and tip conveying section 20 is arranged to be capable of receiving the pipette tip 2 from the shoot 40c when the detection strip 24 of the emergency specimen and tip conveying section 20 is detected by the light shielding sensor 25, as shown in FIG. 3.

The pipette tip 2 mounted on the tip installing part 23b of the conveying rack 23 is conveyed to a position corresponding to the attachment position 1b (see FIG. 1) of the specimen dispensing arm 50. As shown in FIG. 28, the distal end 54b of the nozzle portion 54a of the arm part 54 is press fit into the attachment part 2c of the pipette tip 2 by moving the arm part 54 downward after turning the nozzle portion 54a of the arm part 54 of the specimen dispensing arm 50 to the attachment position 1b (see FIG. 1). The pipette tip 2 is thereby supplied from the pipette tip supply device 30 to the specimen dispensing arm 50.

(Dispensing Operation)

The specimen dispensing arm 50 turns the nozzle portion 54a of the arm part 54 to the suction position 1a (see FIG. 1) or to the attachment position 1b (see FIG. 1), and then, moves the arm part 54 downward so as to suck the specimen in the test tube 3 conveyed to the suction position 1a by the specimen conveying section 10 or the specimen in the test tube 3 conveyed to the attachment position 1b by the emergency specimen and tip conveying section 20 into the pipette tip 2 attached to the distal end 54b of the nozzle portion 54a with negative pressure. Then, the arm part 54 is moved upward to turn the nozzle portion 54a of the arm part 54 to the holding portion 81b of the rotating table part 81a of the primary reaction section 81, and then, the arm part 54 is moved downward to discharge the specimen into the cuvette 8 (see FIG. 17) held by the holding portion 81b of the rotating table part 81a of the primary reaction section 81.

(Pipette Tip Releasing Operation)

Figure 30:
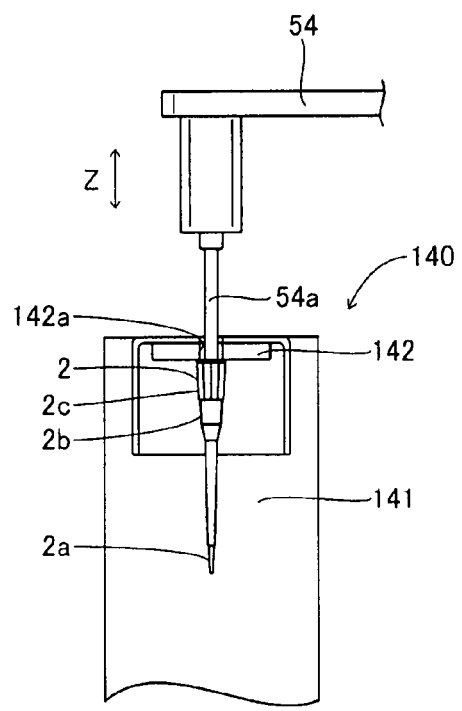
FIG. 30 is a side view for explaining the releasing operation of the pipette tip attached to the specimen dispensing arm of the immune analyzing device shown in FIG. 1.
Figure 31:
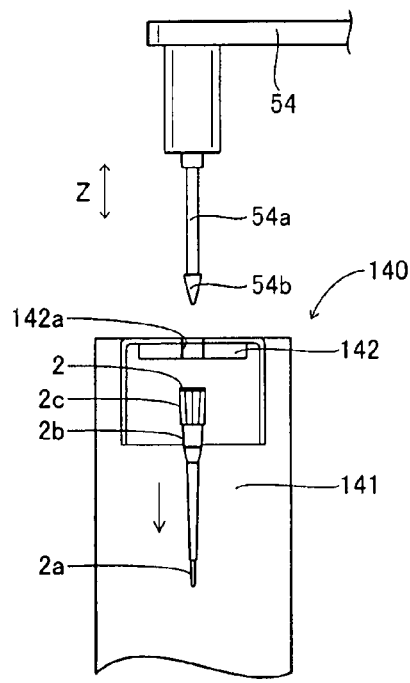
FIG. 31 is a side view for explaining the releasing operation of the pipette tip attached to the specimen dispensing arm of the immune analyzing device shown in FIG. 1.

FIGS. 29 to 31 are side views for explaining the releasing operation of the pipette tip attached to the specimen dispensing arm of the immune analyzing device shown in FIG. 1. Subsequently, the releasing operation of the pipette tip attached to the specimen dispensing arm will be explained with reference to FIGS. 29 to 31.

Firstly, the arm part 54 to which the used pipette tip 2 is attached is moved downward, and the arm part 54 is turned such that the nozzle portion 54a of the arm part 54 is fitted into the cut-out part 142a of the release strip 142 of the tip releasing section 140 as shown in FIG. 29. The arm part 54 is moved upward from this state, whereby the lower surface of the release strip 142 of the tip releasing section 140 comes in contact with the upper surface of the attachment part 2c of the pipette tip 2 as shown in FIG. 30. Then, the pipette tip 2 is released from the distal end 54b of the nozzle portion 54a of the arm part 54 by moving the arm part 54 upward as shown in FIG. 31.

In the present embodiment, the push-up plate 373g that pushes up the pipette tip 2 to the sending position (see FIG. 21) from the receiving position (see FIG. 16) is provided so as to be adjacent to the wall section 374 as described above. Further, when the push-up plate 373g is located at the sending position, at least a part of the upper end portion 374a of the wall section 374 is located below the pipette tip 2 on the slanted surface part 373h of the push-up plate 373g. Moreover, since the upper end portion 374a of the wall section 374 is inclined downward along the X2 direction, only the attachment part 2c or distal end 2a of the pipette tip 2 placed onto the slanted surface part 373h of the push-up plate 373g can be pushed up to the position upper than the upper end portion 374a of the wall section 374 by the portion of the upper end portion 374a of the wall section 374 that becomes lower than the slanted surface part 373h of the push-up plate 373g due to the relative inclination, during the process of moving the push-up plate 373g from the receiving position to the sending position. Specifically, even when two pipette tips 2 are placed onto the slanted surface part 373h of the push-up plate 373g as vertically overlapped, only the attachment part 2c or distal end 2a of the upper pipette tip 2 can be pushed up to the position upper than the slanted surface part 373h of the wall section 374 by the portion of the upper end portion 374a of the wall section 374 that becomes lower than the slanted surface part 373h of the push-up plate 373g due to the relative inclination. Therefore, as one end portion (e.g., attachment part 2c) of the pipette tip 2 goes over the upper end portion 374a of the wall section 374 to be sent to the wall section 374, the other end portion (e.g., distal end 2a) turns to be moved in the direction opposite to the wall section 374, resulting in that the upper pipette tip 2 placed onto the slanted surface part 373h of the push-up plate 373g as overlapped becomes unbalanced to be sent to the wall section 374 or to the storage section 372 from the slanted surface part 373h of the push-up plate 373g. Thus, even when two pipette tips 2 are placed onto the slanted surface part 373h of the push-up plate 373g as vertically overlapped, it is prevented that both of two pipette tips 2 placed onto the slanted surface part 373h of the push-up plate 373g as overlapped are simultaneously sent to the wall section 374. As a result, the pipette tip 2 can surly be supplied to the wall section 374 one at a time.

In the present embodiment, the moving push-up plate 373g is stopped at the first stopping position or second stopping position, whereby the pipette tip 2 placed onto the slanted surface part 373h of the push-up plate 373g can be brought into more unstable state. As a result, the upper pipette tip 2 of the pipette tips placed as vertically overlapped mostly loses the balance and falls down to the storage section 372, resulting in that the remaining one pipette tip 2 can be pushed up by the push-up plate 373g to be supplied to the movement section 38.

In the present embodiment, since the pipette tip 2 placed onto the slanted surface part 373h of the push-up plate 373g becomes unstable because the thickness T (about 4.0 mm) of the push-up plate 373g is set smaller than the outer diameter R (about 7.0 mm) of the attachment part 2c of the pipette tip 2, it can be prevented that two pipette tips 2 vertically overlapped are pushed up to the sending position with this state without losing balance. As a result, the pipette tip 2 can more surely be supplied to the wall section 374 one at a time.

In the present embodiment, the sort mechanism section 37 is provided with the storage section 372 that is arranged so as to be adjacent to the push-up plate 373g at the upstream side of the push-up plate 373g and has the slanted surface part 372a that is inclined downward toward the push-up plate 373g. This configuration can make two to three pipette tips 2 pushed up by the push-up plate 371g of the cut-to-form mechanism section 371 slip down along the slanted surface part 372a, thereby being capable of easily guiding the pipette tip 2 to the push-up plate 373g.

In the present embodiment, the cut-to-form mechanism section 371 provided with the push-up plate 371g arranged so as to be adjacent to the upstream side of the storage section 372 is provided. Further, the push-up plate 371g is configured to move in the Z direction along the storage section 372 in order to limit the number of plural pipette tips 2 and supply the same to the storage section 372. Therefore, before the pipette tip 2 is supplied by the push-up plate 373g one by one, the pipette tip 2 can be supplied to the push-up plate 373g with the number thereof limited beforehand to two to three. As a result, the number of the pipette tips 2 can be limited stepwisely, whereby one pipette tip 2 can more surely be supplied to the wall section 374.

The device according to the present embodiment has the detection section 41e for detecting the pipette tip 2 sent from the push-up plate 373g to the movement section 38, and the control section 150 that controls the operation of the stepping motor 373a so as to stop the operation of the push-up plate 373g and move the same downward when the detection section 41e detects that the pipette tip 2 is sent from the push-up plate 373g to the movement section 38. Therefore, if the operation of the push-up plate 373g is stopped when one pipette tip 2 is sent to the movement section 38 by the push-up plate 373g, it can be prevented that the second pipette tip 2 is continuously sent to the movement section 38 even when two pipette tips 2 are placed onto the slanted surface part 373h of the push-up plate 373g. As a result, the pipette tip 2 can more surely be supplied to the movement section 38 one at a time.

In the present embodiment, the opening 30c of the chassis 30a is formed at the position above the pipette tips 2 accumulated in the drum 335. Therefore, when the opening of the drum and the opening of the chassis agree with each other, the pipette tips in the drum other than the pipette tips held by the segmenting part are not sent to the conveying path, so that the appropriate amount of pipette tips can be sent to the conveying path.

In the present embodiment, the neutralizing fan 35 is arranged as described above so as to send ionized air to the pipette tip 2 lifted by the segmenting part 335b of the drum 335 through the opening 30c of the chassis 30a and to send the ionized air to the pipette tip 2 sent from the segmenting part 335b to be located at the inclined path 34a of the conveying path 34. This configuration can prevent that the pipette tip 2 is adsorbed to the segmenting part 335b of the tip supply mechanism section 33, conveying path 34, junction member 40, sort mechanism section 37, movement section 38, shoot 40b, movement section 39, and shoot 40c, on the supply path, due to the charged charges on the pipette tip 2, or the pipette tips 2 are adsorbed to each other. Consequently, the pipette tip 2 can smoothly be supplied to the tip installing part 23b of the conveying rack 23 of the emergency specimen and tip conveying section 20.

The device according to the present embodiment is provided with the sort mechanism section 37 for sorting one by one the pipette tip 2 received from the conveying path 34 and the movement sections 38 and 39 for conveying the sorted pipette tip 2 in such a manner that the distal end 2a of the sorted pipette tip 2 is directed downward. Therefore, the pipette tip 2 is sorted one by one and can be supplied with the distal end 2a directed downward. As a result, the supplied pipette tip 2 can easily be attached to the specimen dispensing arm 50 one by one in the immune analyzing device 1 provided with the specimen dispensing arm 50 using the supplied pipette tip 2.

It should be considered that the disclosed embodiment is only illustrative in all aspects, and not restrictive. The scope of the present invention is shown by the claims, not by the explanation of the above-mentioned embodiment, and the present invention includes all modifications equivalent to the claims and within the scope of the claims.

For example, the embodiment described above shows the case where the automatic pipette tip supply device that supplies a disposable pipette tip one by one is applied to an immune analyzing device. However, the present invention is not limited thereto. The present invention is applicable to a device other than the immune analyzing device, so long as it uses a pipette tip.

The embodiment described above shows the case in which the pipette tip 2 pushed up by the push-up plate 371g of the cut-to-form mechanism section 371 is supplied to the push-up plate 373g of the cut-to-form mechanism section 373 through the slanted surface part 372a of the storage section 372. However, the present invention is not limited thereto. The pipette tip 2 pushed up by the push-up plate 371g of the cut-to-form mechanism section 371 may directly be supplied to the push-up plate 373g of the cut-to-form mechanism section 373 not through the slanted surface part 372a of the storage section 372.

The embodiment described above shows the case in which the upper end portion 374a of the wall section 374 is downward in the direction of the arrow X2, but the invention is not limited thereto. The slanted surface part 373h of the push-up plate 373g of the cut-to-form mechanism section 373 may be inclined along the direction of the arrow X1 or direction of the arrow X2.

The embodiment described above shows the case in which the upper end portion of the wall section is inclined so as to be downward in the widthwise direction (in the direction of the arrow X2) and the upper end portion of the push-up plate is horizontal in the widthwise direction, but the invention is not limited thereto. For example, the upper end portion of the wall section may be horizontal in the widthwise direction and the upper end portion of the push-up plate may be inclined in the widthwise direction, or the upper end portion of the wall section and the upper end portion of the push-up plate may be inclined in the opposite direction in the widthwise direction. Further, the upper end portion of the wall section is not inclined, but a step may be formed at the middle part in the widthwise direction at the upper end portion of the wall section in such a manner that a part thereof becomes high and the other part becomes low in the widthwise direction. Alternatively, the step described above in the widthwise direction may be formed at the push-up plate.

For example, the embodiment described above shows the case where the pipette tip supply device that supplies a disposable pipette tip one by one is applied to an immune analyzing device. However, the present invention is not limited thereto. The present invention is applicable to a device other than the immune analyzing device, so long as it uses a disposable pipette tip. For example, the pipette tip supply device of the present invention may be used for an analyzing device such as a gene testing device or bacteria testing device. Further, the embodiment described above shows the case in which the pipette tip 2 is used for sucking a specimen such as blood, but the invention is not limited thereto. The pipette tip 2 may be used for sucking liquid such as reagent.

The embodiment described above shows the case in which the segmenting part of the drum scoops up the pipette tip accumulated at the lower part and conveys the scooped pipette tip to the conveying path by the rotation of the drum, but the invention is not limited thereto. A predetermined amount of pipette tips may be sent, from the portion where the pipette tips are accommodated, to the conveying path by lifting up the same like the cut-to-form mechanism section at the sort mechanism section in the present embodiment. Further, the above-mentioned embodiment shows the configuration having the drum rotating about the horizontally extending center axis (rotational axis) defined as a rotational center, wherein the pipette tip in the drum is scooped up by the segmenting part with the rotation of the drum. However, in the configuration described above, the drum may not necessarily be the one rotating about the horizontal axis, but the drum having the rotational axis in the diagonal direction may be employed.

The above-mentioned embodiment describes the configuration in which the segmenting part scoops up the pipette tip by the rotation of the drum (accommodating chamber). In this configuration, the accommodating chamber is not necessarily cylindrical, but it may have a polygonal prism shape. Further, the above-mentioned embodiment describes the case in which the segmenting part 335b attached to the inner peripheral surface 335d and the inner wall 335e of the drum 335 scoops us the pipette tips 2 accumulated in the accommodating part 335a of the drum 335 by the rotating movement of the segmenting part 335b with the rotation of the drum 335. However, the present invention is not limited thereto. The configuration may be employed in which the segmenting part that is not attached to the inner peripheral surface or inner wall of the drum rotates and moves in the drum without causing the rotation of the drum. For example, a rotational axis horizontally passing the center of the drum may be provided, and the rotational axis and segmenting part may be connected by a spoke. Moreover, in the above-mentioned embodiment, two openings 335c and two segmenting parts 335b are provided about the rotational axis of the drum 335 at an interval of 180 degrees at the inside of the drum 335. However, the present invention is not limited thereto. Three openings and three segmenting parts may be provided about the rotational axis of the drum 335 at an interval of 120 degrees. The above-mentioned embodiment uses the segmenting part 335b that can scoop up five to fifteen pipette tips 2. However, the present invention is not limited thereto. A segmenting part that can scoop up fifteen or more pipette tips may be used, or a segmenting part that can scoop up only four or less pipette tips may be used.

The embodiment described above uses the neutralizing fan 35 as a neutralizing part for removing charged charges of the pipette tip 2. However, the present invention is not limited thereto. The charged charges on the pipette tip may be removed by bringing a conductive member into contact with the pipette tip.

The embodiment described above shows the case in which the pipette tip 2 is held by the feed screw 395 and wall section 396 at the movement section 39 so as to be conveyed. However, the present invention is not limited thereto. A pipette tip 2 that is sorted one by one may be sandwiched by two belts to be held, and transported one by one.

The above-mentioned embodiment shows the case in which plural refilling pipette tips are accommodated into the tip refill section, and then, plural pipette tips are inputted into the drum from the tip refill section via the shoot. However, the present invention is not limited thereto. Plural pipette tips may directly be inputted into the drum. Subsequently, a cuvette supply device according to a second embodiment of the invention will be explained. This cuvette supply device is such that, for example, in the pipette tip supply device 30 shown in FIG. 10, the sort mechanism section 37 for sorting the pipette tips is changed to a cuvette sort mechanism section 66 shown in FIG. 39, a cuvette is inputted into the tip refill section 31 (see FIG. 5) of the pipette tip supply device 30, and cuvettes are accommodated into the drum 335 (see FIG. 5). The cuvette supply device having the configuration described above is arranged instead of the cuvette supply section 70 in FIG. 1.

Figure 39:
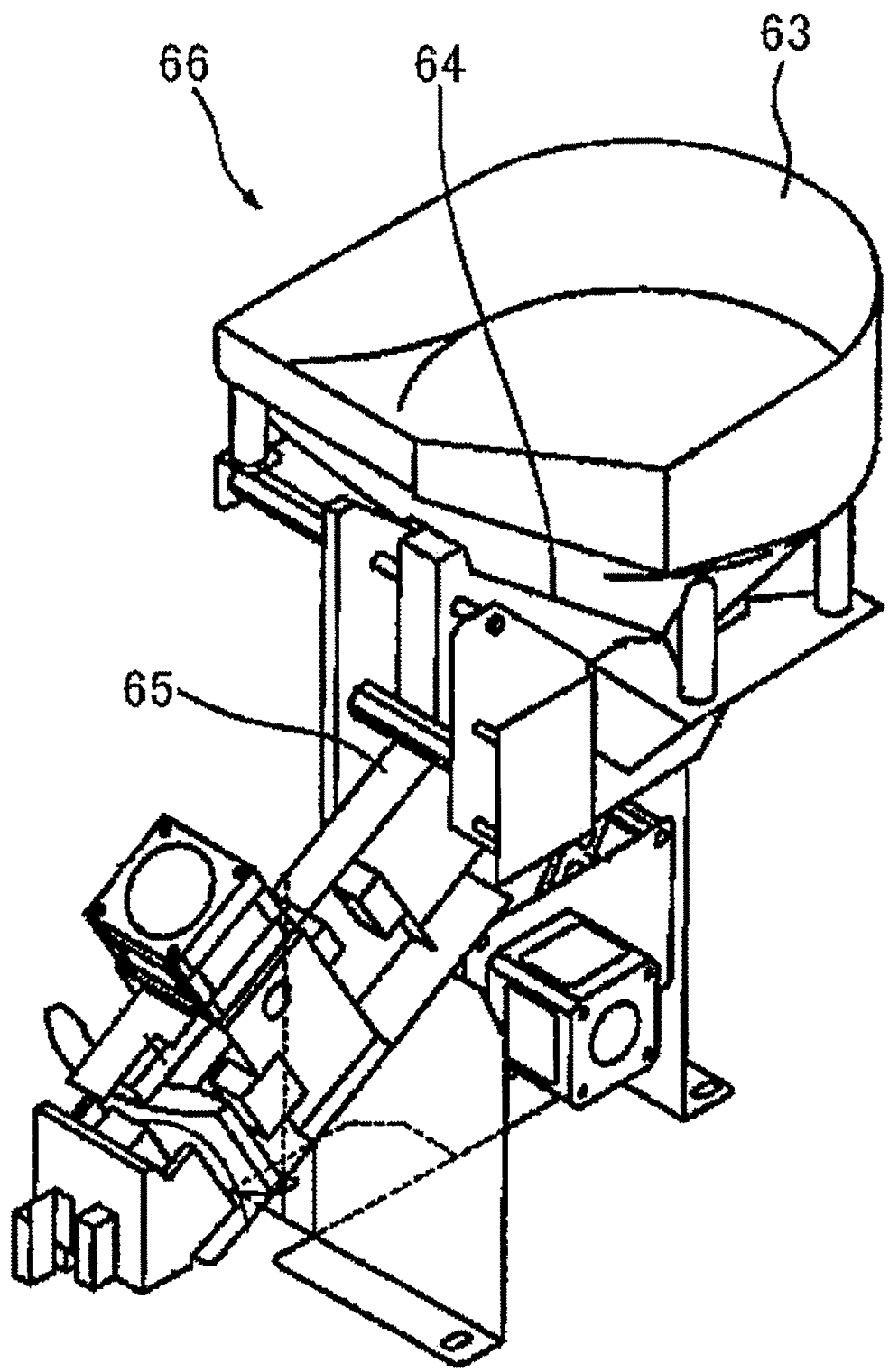
FIG. 39 is a perspective view showing a cuvette sort mechanism section for sorting a cuvette.
Figure 40:
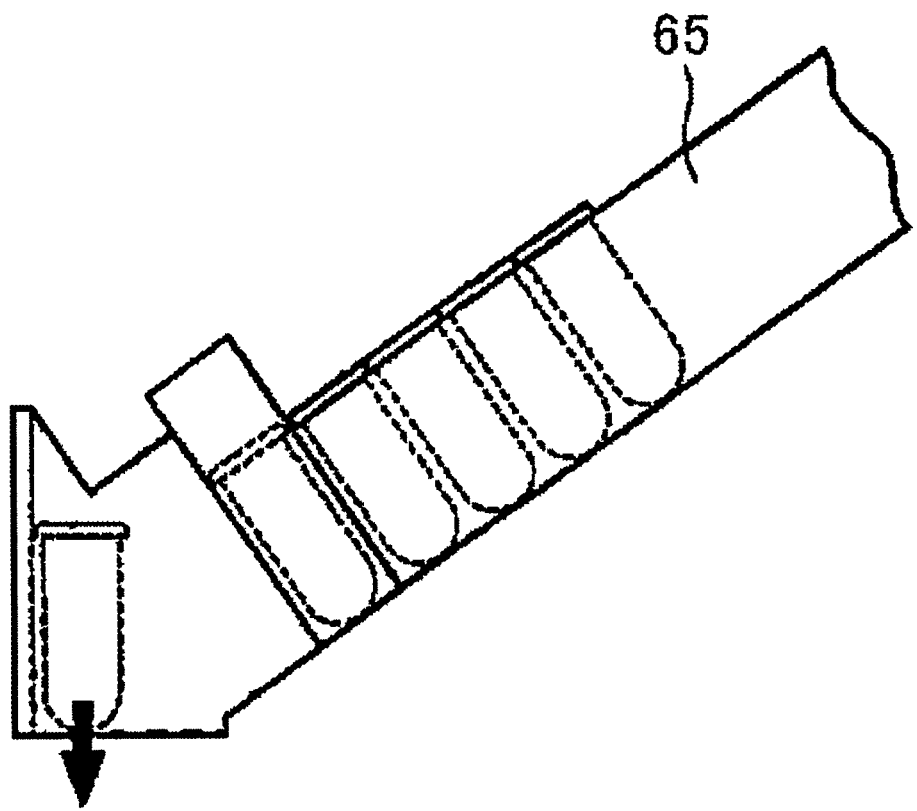
FIG. 40 is a side view showing a movement section of the cuvette sort mechanism section shown in FIG. 39.

FIG. 39 is a perspective view showing one example of the cuvette sort mechanism section 66. The cuvette sort mechanism section 66 is configured to sort a predetermined amount of cuvettes one by one, and convey the sorted cuvette to a predetermined position. The cuvette sort mechanism section 66 has a storage section 63 for storing a cuvette provided with a passing hole for passing a cuvette one by one, a guide rail 64 that can move up and down, wherein one end thereof closes the passing hole when it is at the upper position and it receives the cuvette one by one from the passing hole and guides the same when it moves to the lower position, and a movement part 65 for conveying the cuvette. FIG. 40 is a side view showing the movement part 65. In this cuvette supply device, a predetermined amount of cuvettes are conveyed from the drum 335 to the storage section 63 of the cuvette sort mechanism section 66. Then, the predetermined amount of conveyed cuvettes are guided one by one by the guide rail 64, and the guided cuvette is conveyed to a predetermined position by the movement part 65 as shown in FIG. 40.

What is claimed is:

1. A device for detecting a target substance in a sample, the device comprising:
    a dispensing arm for dispensing a sample using a pipette tip;
    a pipette tip supply device for supplying the pipette to the dispensing arm;
    a preparing section configured to prepare an analyzing sample by using a reagent and the sample dispensed by the dispensing arm attaching the pipette tip; and
    a detecting section for detecting a target substance in the analyzing sample prepared by the preparing section;
    wherein the supply device comprises:
    a storage section configured to store a plurality of pipette tips, each of the pipette tips having a distal end, body part and an attachment part which is attached to the dispensing arm;
    a sort section including a push-up plate to push up a pipette tip supplied from the storage section and a wall section fixedly arranged adjacent to the push-up plate and at a downstream side of the push-up plate, wherein the push-up plate is configured to send the pipette tips one-by-one over the wall section,
    wherein the push-up plate has a slanted surface part that is defined by a plane in a width direction and inclined in a thickness direction and is configured to vertically move along the wall section between a receiving position for receiving the supplied pipette tip and a sending position for sending the supplied pipette tip over the wall section, and an upper end portion of the wall section is inclined in a thickness direction of the wall section and has a slanted surface part inclined in a width direction of the wall section;
    a movement section configured to transport the sent pipette tip to a pipette tip receiving position;
    a conveying rack having a hole for holding the transported pipette tip; and
    a slide rail configured to move the conveying rack and arranged between the pipette tip receiving position and an attachment position for attaching the pipette tip to the dispensing arm, wherein the conveying rack is movable along the slide rail between the pipette tip receiving position and the attachment position;
    wherein the dispensing arm is configured to attach the pipette tip conveyed by the conveying rack at the attachment position.

2. The device according to claim 1, wherein the movement section comprises a shoot configured to guide the transported pipette tip to the pipette tip receiving position.

3. The device according to claim 2, wherein the movement section comprises a feed screw for transporting the pipette tip to the shoot.

4. The device according to claim 3, wherein the feed screw has a groove part having a width smaller than an outer diameter of the attachment part of the pipette tip and greater than an outer diameter of the body part of the pipette tip.

5. The device according to claim 1, wherein an upper end portion of the wall section is inclined in a thickness direction of the wall section and has a slanted surface part inclined in a width direction of the wall section and an additional slanted surface part defined by a plane in the width direction that abuts the slanted surface part and that is parallel with the slanted surface part of the push-up plate,
    wherein the additional slanted surface part of the wall section and the slanted surface part of the push up plate are in the same plane in the sending position.

6. The device according to claim 1,
    wherein
    the thickness of the push-up plate is smaller than the diameter of the attachment part of the pipette tip.

7. The device according to claim 1, further comprising a slope inclined downward toward the push-up plate is arranged between the storage section and the push-up plate, wherein the slope conveys the supplied pipette tips to the push-up plate.

8. The device according to claim 7, further comprising:
    a discharging mechanism section for discharging the supplied pipette tips, the discharging mechanism comprising a turning member constituting the slope.

9. The device according to claim 1,
    wherein
    the sort section further comprises an additional push-up plate arranged at the upstream side of the push-up plate, wherein the additional push-up plate is configured to vertically move in order to supply the pipette tip to the push-up plate.

10. The device according to claim 1, further comprising:
    a detection sensor configured to detect whether the pipette tip is present or not in the movement section; and
    a control section configured to control the sort section so as to stop vertically moving of the push-up plate when the pipette tip is present in the movement section, and to control the sort section so as to perform vertically moving of the push-up plate when the pipette tip is not present in the movement section.

11. A device for detecting a target substance in a sample, the device comprising:
- a dispensing arm for dispensing a sample using the pipette tip;
- a pipette tip supply device for supplying the pipette to the dispensing arm;
- a preparing section configured to prepare an analyzing sample by using a reagent and the sample dispensed by the dispensing arm attaching the pipette tip; and
- a detecting section for detecting a target substance in the analyzing sample prepared by the preparing section;
- wherein the supply device comprises:
- a storage section configured to store a plurality of pipette tips, each of the pipette tips having a distal end, body part and an attachment part which is attached to the dispensing arm;
- a sort section including a push-up plate to push up a pipette tip supplied from the storage section and a wall section fixedly arranged adjacent to the push-up plate and at a downstream side of the push-up plate, wherein the push-up plate is configured to send the pipette tips one-by-one over the wall section,
- wherein an upper end portion of the wall section is inclined in a thickness direction of the wall section and has a slanted surface part inclined in a width direction of the wall section and an additional slanted surface part being horizontal in the width direction;
- a movement section configured to transport the sent pipette tip to a pipette tip receiving position; and
- a conveying rack configured to hold the transported pipette tip; and
- a slide rail configured to move the conveying rack and arranged between the pipette tip receiving position and an attachment position for attaching the pipette tip to the dispensing arm, wherein the conveying rack has a hole for holding the pipette tip which has been received at the pipette tip receiving position, and the conveying rack is movable along the slide rail between the pipette tip receiving position and the attachment position;
- wherein the dispensing arm is configured to attach the pipette tip conveyed by the conveying rack at the attachment position.

12. The device according to claim 11, wherein the push-up plate has a slanted surface part that is defined by a plane in a width direction and inclined in a thickness direction, and is configured to vertically move along the wall section between a receiving position for receiving the supplied pipette tip and a sending position for sending the supplied pipette tip over the wall section.

13. The device according to claim 12, wherein the thickness of the push-up plate is smaller than the diameter of the attachment part of the pipette tip.

14. The device according to claim 11, further comprising a slope inclined downward toward the push-up plate is arranged between the storage section and the push-up plate, wherein the slope conveys the supplied pipette tips to the push-up plate.

15. The device according to claim 11, further comprising:
- a detection sensor configured to detect whether the pipette tip is present or not in the movement section; and
- a control section configured to control the sort section so as to stop vertically moving of the push-up plate when the pipette tip is present in the movement section, and to control the sort section so as to perform vertically moving of the push-up plate when the pipette tip is not present in the movement section.

16. The device according to claim 11, wherein the movement section comprises a shoot configured to guide the transported pipette tip to the pipette tip receiving position and a feed screw for transporting the pipette tip to the shoot.

17. The device according to claim 16, wherein the feed screw has a groove part having a width smaller than an outer diameter of the attachment part of the pipette tip and greater than an outer diameter of the body part of the pipette tip.

* * * * *